US006965240B1

(12) United States Patent
Litton et al.

(10) Patent No.: US 6,965,240 B1
(45) Date of Patent: Nov. 15, 2005

(54) APPARATUS AND METHODS FOR ANALYZING PARTICLES USING LIGHT-SCATTERING SENSORS AND IONIZATION SENSORS

(75) Inventors: Charles D. Litton, Pittsburgh, PA (US); Jon C. Volkwein, Canonsburg, PA (US); William H. Schiffbauer, Connellsville, PA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/401,980

(22) Filed: Mar. 27, 2003

Related U.S. Application Data

(60) Provisional application No. 60/369,537, filed on Apr. 1, 2002.

(51) Int. Cl.[7] .............................................. G01N 27/62
(52) U.S. Cl. ...................... 324/464; 324/448; 73/28.04
(58) Field of Search ............................... 324/464, 448, 324/449, 450, 71.4; 73/28.01–28.04, 118; 250/287; 356/335

(56) References Cited

U.S. PATENT DOCUMENTS

| | | | | |
|---|---|---|---|---|
| 1,100,171 A | * | 6/1914 | Brown ....................... 73/28.01 |
| 3,794,909 A | * | 2/1974 | Smith ......................... 324/464 |
| 4,764,758 A | | 8/1988 | Skala ......................... 340/627 |
| 4,916,384 A | * | 4/1990 | Ishida ....................... 324/71.4 |
| 5,279,146 A | | 1/1994 | Asano et al. ............... 73/28.04 |
| 5,498,271 A | | 3/1996 | Marple et al. ................ 55/321 |
| 5,571,945 A | | 11/1996 | Koutrakis et al. ......... 73/28.03 |
| 5,805,283 A | | 9/1998 | Ludman et al. ............. 356/484 |
| 5,932,795 A | | 8/1999 | Koutrakis et al. ......... 73/28.01 |
| 6,181,419 B1 | | 1/2001 | Snelling et al. ............. 356/335 |
| 6,239,428 B1 | | 5/2001 | Kunz ......................... 250/287 |
| 6,435,019 B1 | * | 8/2002 | Vojtisek-Lom ............. 73/118.1 |

OTHER PUBLICATIONS

Litton, "Fractal Properties of Smoke Produced from Smoldering and Flaming Fires," in Proceedings of Symposium on Combustion, Fire and Exposion, and Alternative Fuels, ASME International Mechanical Engineering Congress and Exposition (Dallas, TX, Nov. 16-21, 1997).

Litton et al., "The Role of Radiation Absorption in Defining Explosibility of Coal/Rock Dust Mixtures," in Proceedings of the 26th International Symposium on Combustion (Naples, Italy, 1996), pp. 1571-1577, no month available.

Litton, "The Use of Light Scattering and Ion Chamber Responses for the Detection of Fires in Diesel Contaminated Atmospheres," *Fire Safety Journal* 37:409-425 (2002), no month available.

(Continued)

*Primary Examiner*—Vincent Q. Nguyen
(74) *Attorney, Agent, or Firm*—Klarquist Sparkman LLP

(57) ABSTRACT

Apparatus and methods are disclosed for analyzing particles, such as coarse particulates, fine particulates (e.g., diesel particulate matter), and combustion aerosols, using light-scattering sensors and/or ionization-type sensors. In one disclosed embodiment, a particle monitor includes an ionization module and a controller adapted to receive an output signal from the ionization module. The controller is operable to translate the output signal into the mass concentration of particulate matter within the ionization chamber. In another embodiment, a particle monitor includes a light-scattering sensor and an ionization sensor. The monitor is configured to measure separate mass concentrations of sub-micrometer particles and larger dust particles in an atmosphere having both types of particles.

18 Claims, 11 Drawing Sheets

OTHER PUBLICATIONS

Litton, "Studies of The Measurement of Respirable Coal Dusts and Diesel Particulate Matter," *Meas. Sci. Technol.* 13:365-374 (2002), no month available.

"Fundamental Scattering Properties of Respirable Dusts and Suspended Particulate Matter," website: www.cdc.gov/niosh/mining/comp2000/fspor.html, 3 pages (2000). Feb. 2000.

* cited by examiner

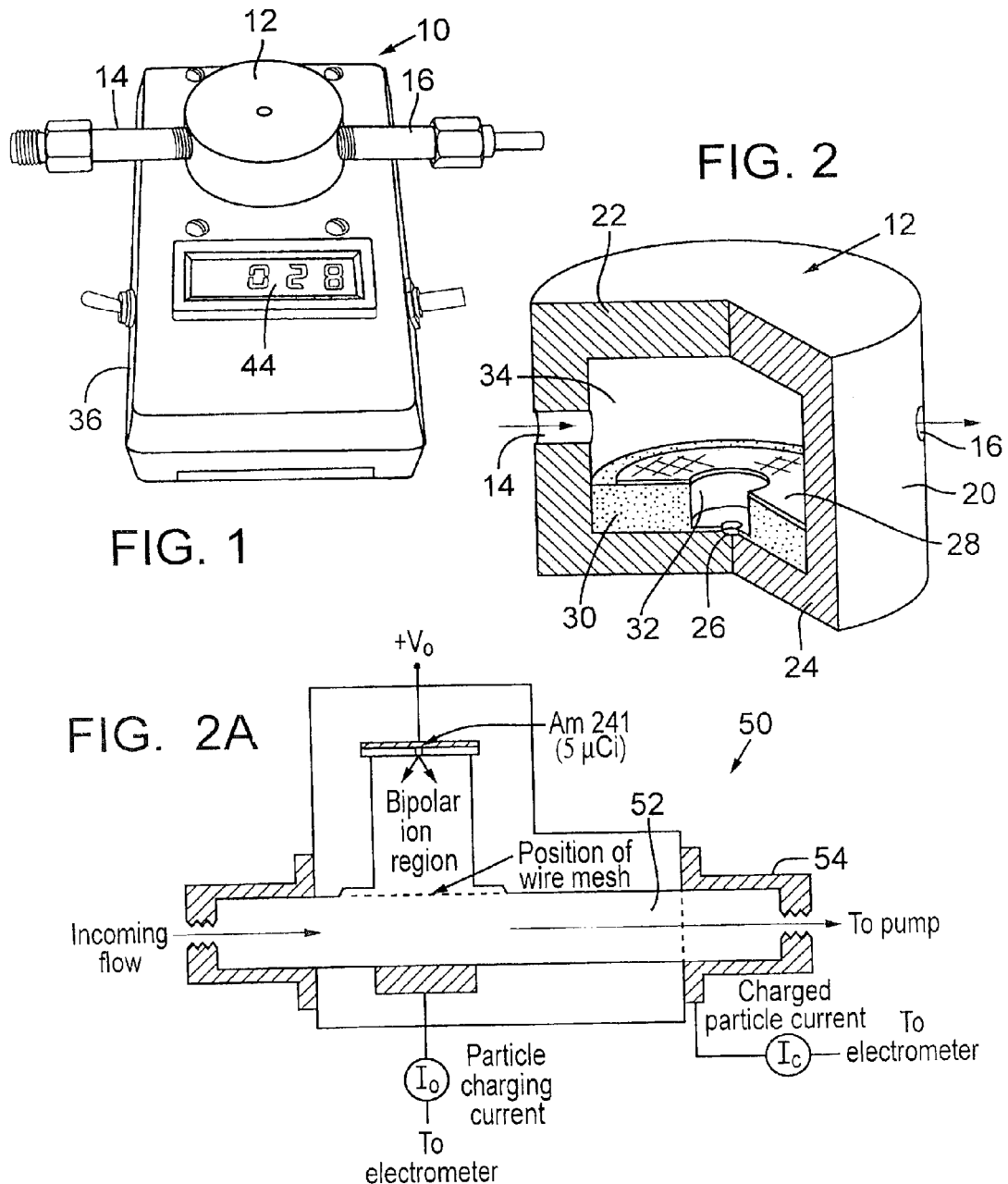

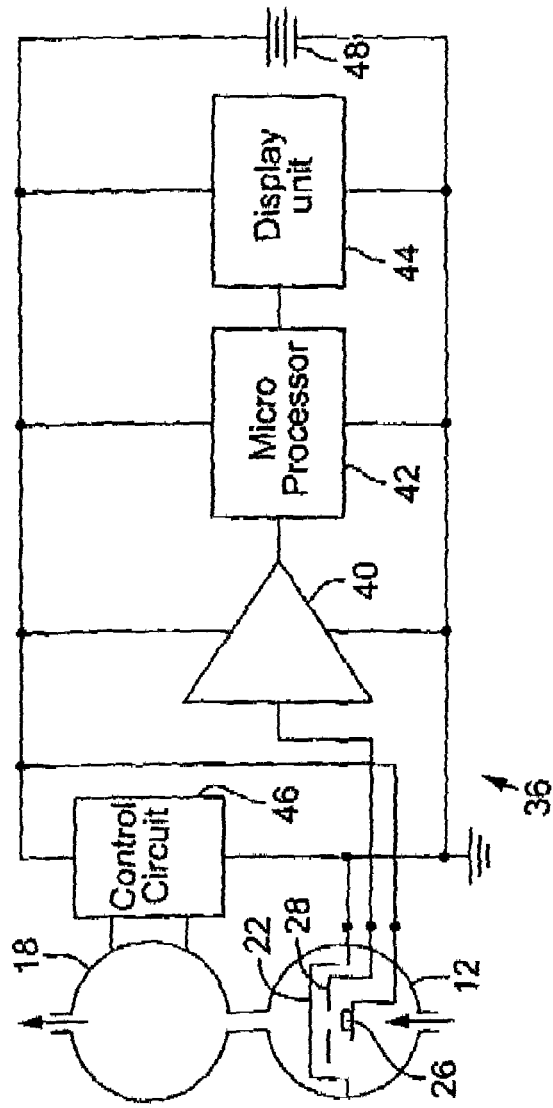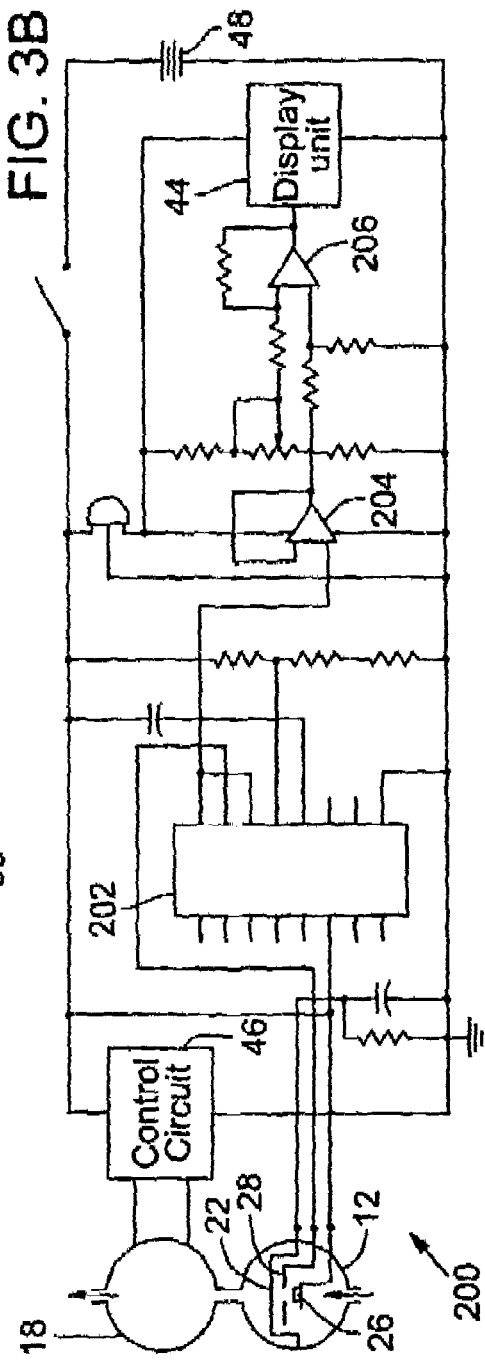

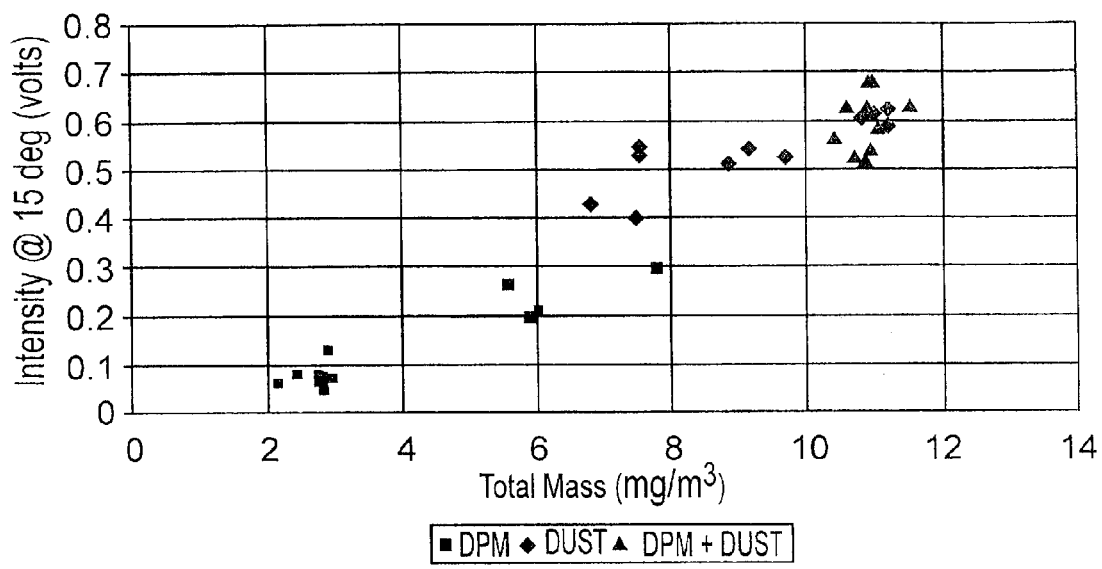

APPARATUS AND METHODS FOR ANALYZING PARTICLES USING LIGHT-SCATTERING SENSORS AND IONIZATION SENSORS

CROSS-REFERENCE TO RELATED APPLICATION

This application claims priority to U.S. Provisional Application Ser. No. 60/369,537, filed Apr. 1, 2002, which is incorporated herein by reference.

FIELD

The present disclosure concerns apparatus and methods for analyzing particles, such as coarse particulates (e.g., respirable dusts), fine particulates (e.g., diesel particulate matter), and combustion aerosols, using light-scattering sensors and/or ionization-type sensors.

BACKGROUND

Coal workers' pneumoconiosis (CWP), or "black lung," is a major health problem resulting from prolonged exposure to respirable coal dusts (dusts with mass mean diameters typically less than 10 $\mu$m). To reduce this problem and provide protection against the occurrence of CWP, current coal mining regulations require that personnel exposure to respirable coal mine dusts be limited to an eight hour time weighted average that does not exceed 2.0 mg/m$^3$.30 C.F.R. § 70.100 (1995).

The standard measurement technique for this determination is continuous sampling of the mine atmosphere through a small, 10 mm cyclone at a nominal flow rate of 2.0 l pm. While this is the generally accepted standard technique for determining respirable dust concentrations, such determinations are cumbersome and time-consuming to complete. As a result, alternative approaches to the measurement of respirable dust concentrations are being studied for their adequacy and accuracy.

In addition, many mines use diesel engines extensively, and the use of diesel engines makes the measurement more complex for a number of reasons. First, the particles deposited on a filter of a conventional measuring device are due both to diesel particulate matter (DPM) and respirable dust, and there is no simple technique to determine their relative contributions to the total mass deposited. Second, since there are significant and different adverse health effects related to DPM (DPM is a suspected carcinogen), the maximum allowable time weighted average concentration for DPM is a factor of 10 lower than that for respirable dust.

Consequently, it is helpful not only to be able to determine the airborne mass concentrations of both DPM and respirable dust, but DPM concentrations need to be measured at significantly lower concentrations. For DPM, the current standard is NIOSH 5040, which is based upon the determination of elemental carbon and organic carbon. NIOSH Manual of Analytic Methods, 4$^{th}$ ed., DHHS (NIOSH) Publication 94–113, Edited by M. E. Cassinelli and P. F. O'Connor (August 1994). However, the chemical composition of DPM may contain significant components of volatile organic compounds, as great as 55 to 60%, so that under some conditions of diesel operation, these standard determinations may not be valid.

Various techniques have been proposed and studied to address these measurement problems. One technique involves the measurement of the pressure drop across a filter onto which particles are deposited by applying of D'Arcy's Law for flow through a porous bed of particles, where the pressure drop across the particle bed, or layer, is a function of the particle concentration and size. See, Volkwein, J. C., Schoeneman, and Page, S. J., *Laboratory Evaluation of Pressure Differential Based Respirable Dust Detector Tube*, Appl. Occ. & Enviro. Hyg., Vol. 15, No. 1, pp. 158–164 (2000).

While this technique appears to work reasonably well for samples that contain no DPM, the presence of even minute quantities of DPM renders the technique unreliable. Even for pure respirable dust samples, significant variations in the pressure drop per unit mass, due most probably to differing particle size distributions, can occur, often resulting in meaningless or skewed measurements.

Another technique involves aerodynamic separation of DPM and respirable dusts. This approach has shown that, typically, particles with diameters less than about 0.7 $\mu$m are the products of diesel combustion while larger particles are due to respirable dusts, although in the region of particle diameters between 0.7 $\mu$m and 1.0 $\mu$m, overlap between the two sources of particles often occurs which makes the determination of individual mass concentrations difficult. In addition, even simple aerodynamic separation techniques require not only very precise flow control but also result in additional filter mass measurements that are even more cumbersome and time-consuming to complete.

Continuous, real-time mass measurements using devices, such as a Tapered Element Oscillating Microbalance (TEOM), have also been proposed for monitoring either DPM or respirable dusts. However, such devices are incapable of discriminating between the two when both exist simultaneously. In addition, while the extension of these continuous, real-time measurement techniques to individual personnel monitoring is feasible, the cost of such devices becomes a major concern.

The use of light scattering as a technique for measuring aerosol and/or respirable dust concentrations is known. Light scattering is attractive as a measurement technique because it is simple and generally inexpensive to implement. Currently, there exist several instruments that are available commercially that utilize this technique, although significant differences exist among the various instruments. Some utilize angular intensities measured at a forward angle of around 12°, while some measure the intensity in the angular range of 16° to 18°. Another known light-scattering instrument measures the intensity over the angular range of 45° to 90° with a maximum sensitivity at around 60°.

Most light-scattering devices use a light source with a wavelength of about 900 nm. However, some of these devices become very sensitive to particle size distributions, or average particle diameters, while some become sensitive to the chemical composition of the scattering particles. These effects can introduce unacceptable errors in the determination of mass concentration. In addition, a major criticism of light scattering is that it is not a direct mass measurement. Rather, mass concentrations are inferred based upon some method of calibration, yet because of particle size, chemical composition, or some other effect, the calibration may not be sufficient to yield accurate determinations of mass concentration over a broad range of aerosol or respirable dust characteristics.

Thus, it would be desirable to determine the combinations of scattering angle and light-source wavelength where the effects of particle size and chemical composition are either negligible or minimal, so as to enable accurate measurements of mass concentrations of particulates, such as respirable dusts, with a light-scattering device.

A related problem encountered in mining environments is that conventional fire sensors that detect the smoke and gases produced during the early stages of developing fires are often compromised by the presence of DPM (as well as background levels of other aerosols or gases) that mimic the signatures of developing fires, often resulting in frequent false, or nuisance, sensor alarms. When the frequency of false alarms is high, the tendency is to either ignore sensors, or to de-energize the sensors, with the potentially catastrophic consequence that an actual fire is not detected.

A commonly used type of smoke detector utilizes light scattering (discussed above) as a technique for detection of developing fires. Currently, there exist many such commercially available detectors that utilize this technique, generally referred as light-scattering smoke detectors or photoelectric smoke detectors. Significant differences exist among the various detectors, for example, angle(s) for detection and light source wavelength.

Another type of smoke detector is an ionization-type smoke detector, which has been used routinely as an early-warning fire sensor since the mid 1970's. Typically, an ionization-type detector comprises an ionization chamber in which there is disposed a source of ions, such as a very low-level radioactive source of Americium 241 (Am 241). Am 241 decays via the emission of alpha particles (He atoms), and as these particles traverse the air space between two field electrodes, both positive and negative ions are created. The positive ions drift to the negative electrode while the negative ions drift to the positive electrode. This separation of ions, coupled with the geometry of the chamber, creates a space charge that distorts the electric field and electric potential within the ion chamber. A third, sensing electrode typically is located between the positive and negative electrodes at a position where the electric potential reaches its maximum distortion.

When smoke enters the air space between the electrodes, the positive and negative ions rapidly attach to the smoke particles, depleting the ion concentrations, which in turn reduce the distortion of the electric potential, causing the potential at the sensing electrode to increase. This change in electric potential provides a measurable indication of the presence of smoke.

While both light-scattering smoke detectors and ionization-type smoke detectors are widely recognized as a useful and inexpensive means in detecting airborne smoke indicative of a fire, the presence of background aerosols and gases, typical in mining and industrial environments, interferes with the ability of conventional detectors to accurately detect smoke.

A significant level of research is being done to address this problem. For smoke, efforts continue to more accurately and completely define the properties of smoke produced from different sources, and to develop improved techniques for smoke measurement. For example, efforts have been made to characterize the signatures of interfering sources using multi-sensor arrays coupled with neural networks, or other multi-signature alarm algorithms.

However, the use of these multi-sensor approaches are generally application-specific in that different applications may require different sensors, and the necessary algorithms can vary significantly from one application to the next. In some of these approaches, it is not only the relative signals from different sensors, but also the manner in which these signals vary with time, that allow for discrimination between smoke and interfering background particulates. In underground mine applications, the use of multi-sensor packages and software to process the signals and make decisions increases the complexity and cost of the system, and necessitates increased system maintenance and sensor replacement.

Therefore, it would be desirable if conventional light-scattering and ionization-type detectors could be configured to discriminate between aerosols produced from fires and common, interfering aerosols and/or gases, such as DPM or any of various other sub-micrometer particles.

SUMMARY

The present disclosure concerns apparatus and methods for analyzing particles, such as coarse particulates, fine particulates, and combustion aerosols, using light-scattering sensors and/or ionization-type sensors.

As used herein, the term "respirable dusts" refers to coarse particulates, which typically are about 1 micron or larger in size. The term "sub-micrometer particles" refers to fine particulates, which typically are less than 1 micron in size.

According to one aspect, a particle analyzer includes an ionization-type sensor for measuring mass concentrations of sub-micrometer particles, such as diesel particulate matter. The particle analyzer also may include a light-scattering sensor for use in cooperation with the ionization-type sensor for measuring mass concentrations of respirable dust and sub-micrometer particles, such as diesel particulate matter, in atmospheres containing both types of particles. The light-scattering sensor may include a light-detecting sensor positioned to detect scattered light at an angle such that the intensity of the scattered light varies substantially linearly with mass concentrations being measured, and is independent of particle size and dust volatility. For example, it was found that positioning a light-detecting sensor to measure scattering light at an angle in the range of about 15° to 30° in the forward direction was effective to minimize the effects of particle size and dust volatility.

A particle analyzer having both an ionization-type sensor and a light-scattering sensor utilizes the relative sensitivities of the ionization-type sensor and the light-scattering sensor to permit separate measurements of sub-micrometer particles and respirable dust. In one approach, for example, the ionization-type sensor, which is generally non-responsive to respirable dusts, is used to measure the mass concentration of sub-micrometer particles. The light-scattering sensor is used to measure the total particle mass concentration (respirable dust and sub-micrometer particles). The mass concentration of respirable dust is then obtained by subtracting the mass concentration of sub-micrometer particles from the total particle mass concentration.

An ionization-type sensor and a light-scattering sensor also can be implemented in a smoke detector for detecting the presence of aerosols produced by combustion in atmospheres contaminated by background emissions, such as diesel particulate matter. In this configuration, the relative sensitivities of the ionization sensor and the light-scattering sensor to diesel particulate matter, flaming combustion aerosols and smoldering combustion aerosols are utilized to discriminate between the three types of particles, thereby permitting accurate detection of combustion aerosols and/or a determination as to the stage of combustion.

More specifically, and according to one representative embodiment, a monitor for measuring the mass concentration of particulate matter includes an ionization module operable to provide an output signal corresponding to the mass concentration of particulate matter within the ionization module. A controller is adapted to receive the output signal from the ionization module, and operable to translate the output signal into the mass concentration of particulate matter within the ionization chamber.

According to another representative embodiment, a light-scattering module includes a housing configured to receive a flow of particles. A light source is provided for projecting a light beam through the housing. At least one light-detecting sensor is positioned to detect scattered light in the housing at an angle such that the intensity of scattered light varies substantially linearly with the mass concentration of particles in the housing. In disclosed embodiments, the wavelength of the light beam produced by the light source is in the range of about 600 to 635 nm and the light-detecting sensor is positioned to detect scattered light at a forward angle in the range of about 15° to 30°.

According to yet another representative embodiment, a particle monitor includes a light-scattering sensor and an ionization sensor. The monitor is configured to measure separate mass concentrations of respirable dust and sub-micrometer particles, such as diesel particulate matter, in an atmosphere comprising respirable dust and sub-micrometer particles.

In particular embodiments, a housing, adapted to receive a flow of particles, is provided for housing the ionization sensor and the light-scattering sensor. The ionization sensor in one configuration includes an ion source, a sensing electrode and at least one field electrode disposed in the housing. The light-scattering sensor in one configuration includes a light source for projecting a light beam through the housing and at least one light-detecting sensor for detecting scattered light in the housing. Desirably, the light-detecting sensor is positioned to detect scattered light in the housing at an angle such that the intensity of scattered light varies substantially linearly with the mass concentration of particles in the housing.

According to another representative embodiment, the mass concentration of particles is measured in an atmosphere comprising respirable dust and sub-micrometer particles. The method includes measuring the total mass concentration of respirable dust and sub-micrometer particles, such as diesel particulate matter, with a light-scattering device and measuring the mass concentration of sub-micrometer particles with an ionization device. The mass concentration of sub-micrometer particles is then subtracted from the total mass concentration of respirable dust and sub-micrometer particles to obtain the mass concentration of respirable dust.

In another representative embodiment, a method detects aerosols produced by combustion in atmospheres contaminated with diesel particulate matter. The method includes measuring the response of an ionization sensor exposed to the atmosphere and measuring the response of a light-scattering sensor exposed to the atmosphere. The response of the ionization sensor is greater to diesel particulate matter than to combustion aerosols, and the response of the light-scattering sensor is greater to combustion aerosols than to diesel particulate matter. Accordingly, the measured responses can be compared to each other, and a determination can be made as to whether the responses indicate the presence of combustion aerosols in the atmosphere. If the response of the light-scattering sensor is sufficiently greater than the response of the ionization sensor, indicating that combustion aerosols are present, an alarm may be activated.

In one approach, for example, the ratio of the response of the ionization sensor to the response of the light-scattering sensor is compared to a predetermined alarm value. If this ratio is less than the predetermined value, indicating that combustion aerosols are present, an alarm may be activated. In an alternative approach, the ratio of the response of the light-scattering sensor to the response of the ionization sensor is compared to a predetermined value, and an alarm is activated if the ratio exceeds the predetermined value.

These and other features of the invention will be more fully appreciated when the following detailed description of the invention is read in conjunction with the accompanying drawings.

BRIEF DESCRIPTION OF THE DRAWINGS

FIG. 1 is a perspective view of an ionization-type particle monitor according to one embodiment.

FIG. 2 is a schematic, perspective view of the bipolar ionization chamber within the monitor of FIG. 1, shown partially in section to reveal the inside of the chamber.

FIG. 2A is a schematic, vertical cross-sectional view of a unipolar ionization chamber according to one embodiment.

FIG. 3A is an electrical schematic according to one embodiment of the monitor of FIG. 1.

FIG. 3B is an electrical schematic of the monitor of FIG. 1, according to another embodiment.

FIG. 13 is a data graph showing angular intensity measured at 15°, expressed in volts, for respirable coal dust, DPM, and mixtures of DPM and respirable coal dust for the light-scattering module of FIG. 6.

FIG. 14 is a data graph showing angular intensity ratios measured for respirable coal dust, DPM, and mixtures of DPM and respirable coal dust using the light-scattering module of FIG. 6.

FIG. 18 is a data graph showing the average sensitivities of the bipolar ionization chamber of FIG. 2 and the light-scattering module of FIG. 6 for different types of particles.

FIG. 19 is a data graph showing the average ratios, $\Delta CEV/\Delta I(15)$ and $\Delta CEV/\Delta I(30)$, for different types of particles.

DETAILED DESCRIPTION

Figure 4A:
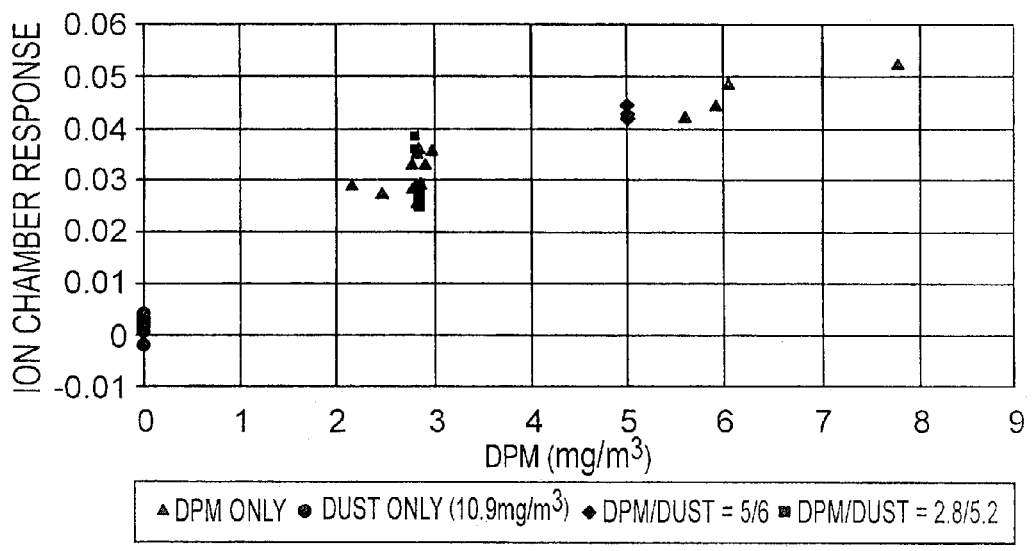
FIG. 4A is a data graph illustrating the current loss ratio parameter, 1-η, measured for respirable coal dust, DPM, and mixtures of DPM and respirable coal dust using the unipolar ionization chamber of FIG. 2A.

In the following detailed description, apparatus and methods are disclosed for analyzing particles, such as respirable dusts, sub-micrometer particles (e.g., diesel particulate matter), and combustion aerosols, using light-scattering sensors and/or ionization-type sensors.

A particle analyzer according to one embodiment may include an ionization-type sensor configured to measure mass concentrations of sub-micrometer particles, such as diesel particulate matter. The particle analyzer also may include a light-scattering sensor for use in cooperation with the ionization-type sensor for measuring separate mass concentrations of respirable dust and sub-micrometer particles in atmospheres containing both types of particles. The light-scattering sensor includes a light-detecting sensor for detecting scattered light, which may be positioned to detect scattered light at an angle such that the intensity of the scattered light varies substantially linearly with mass concentrations being measured, and is independent of dust volatility.

For measuring separate mass concentrations of respirable dust and sub-micrometer particles, the light-scattering sensor is used to measure the total particle mass concentration in the atmosphere (respirable dust and sub-micrometer particles). The ionization-type sensor, which is generally non-responsive to respirable dust, is used to measure the mass concentration of sub-micrometer particles. The mass concentration of respirable particles can be obtained by subtracting the mass concentration of sub-micrometer particles from the total particle mass concentration.

An ionization-type sensor and a light-scattering sensor also can be used to provide a smoke detector having discrimination capabilities for discriminating between diesel particulate matter, smoldering combustion aerosols and flaming combustion aerosols.

More specific configurations and methods embodying one or more of these features are described in the following examples.

Ionization Monitor

Referring first to FIG. 1, there is shown one embodiment of an ionization-type particle monitor 10 configured to measure mass concentrations of sub-micrometer particles, such as diesel particulate matter (DPM). The monitor 10 may be worn by or carried by a user, such as a worker in an underground mine to monitor the mass concentration of DPM in the surrounding atmosphere. Alternatively, the monitor 10 may be placed in a stationary position.

Referring also to FIG. 2, the monitor 10 includes an ionization chamber 12, which is formed with an inlet conduit 14 and an outlet conduit 16. The monitor 10 also includes a housing 36 (FIG. 1) that contains control electronics 38 (FIG. 3A). A pump 18 (FIG. 3A) may be provided to induce a flow of particles suspended in the atmosphere through the ionization chamber 12 from the inlet conduit 14 to the outlet conduit 16.

As best shown in FIG. 2, the ionization chamber 12 is generally cylindrical in shape having a cylindrical side wall 20 bounded by an upper wall 22 and a lower wall 24. The particular shape of the chamber 12, however, is not limited to that of the illustrated embodiment. Accordingly, the chamber 12 may comprise any of various other geometric shapes.

An ion source 26, such as Am241, positioned on the inner surface of the lower wall 24, serves as a source of ions and as a first field electrode for the ionization chamber 12. The upper wall 22 in the illustrated embodiment is made from metal, and thus serves as a second field electrode for the ionization chamber 12. An annular-shaped electrical insulator 30 is disposed on the inner surface of the lower wall 24 so as to separate the interior of the chamber 12 into a first cylindrical-shaped region 32 and a second cylindrical-shaped region 34. A sensing electrode 28 is disposed on the top surface of the insulator 30 for measuring the electric potential in the chamber 12. The sensing electrode 28 is also referred to herein as a "floating" electrode because it measures an electro-static potential in the chamber 12. Desirably, the sensing electrode 28 is positioned in a plane that corresponds approximately to the plane of maximum distortion of potential within the chamber 12.

When particles suspended in the atmosphere enter the ionization chamber 12, positive and negative ions attach to the particles, depleting the ion concentrations, which in turn reduces the distortion of the electric potential, thereby causing the potential at the sensing electrode to increase. The ionization chamber 12 may be referred to as a "bipolar chamber" because both positive and negative air ions are created within the first and second regions 32, 34, respectively.

In alternative embodiments, the ion source and the first field electrode may be separate components. For example, in one alternative configuration, a first field electrode is positioned on the inner surface of the lower wall 24 and a separate ion source is mounted to, or otherwise carried by, the first field electrode. In another embodiment, the second field electrode is a separate component mounted to the inner surface of the top wall. Still alternatively, the chamber 12 may be an open-type chamber, such as used in conventional smoke detectors, having a plurality of apertures or windows formed in the side wall 20 to permit gas to freely flow into the chamber, such as via diffusion or convective air flows. In the latter configuration, the pump 18 would be optional.

FIG. 3A is a schematic diagram illustrating further features of the monitor 10. As shown in FIG. 3A, the ionization chamber 12 is electrically coupled to control electronics 36 (also referred to herein as a "controller" in other embodiments), which in the illustrated configuration include, a sensor-conditioning module 40 (e.g., an amplifier), a microprocessor 42, and a visual display unit 44 (FIGS. 1 and 3A) (e.g., an LCD display). The control electronics 36 also may include a suitable power source 48 (e.g., a battery) for powering the monitor 10, and a pump control circuit 46 electrically connected to the pump 18 for controlling the operation of the pump 18.

The sensor-conditioning module 40 is electrically connected to the sensing electrode 28, which produces an output voltage corresponding to the mass concentration of particles in the ionization chamber 12. The microprocessor 42 receives a conditioned signal (e.g., an amplified signal) from the sensor-conditioning module 40 and translates the signal into the mass concentration of particles in the ionization chamber 12. This value may be displayed on the visual display unit 44. A visual or audible alarm (not shown) or other suitable warning devices may be provided to warn a user if the measured mass concentration of particles exceeds a predetermined value.

FIG. 3B shows another embodiment of an electrical schematic for the monitor 10, indicated generally at 200. Components in FIG. 3A that are identical to corresponding components in FIG. 3B have the same respective reference numerals and are not described further. In this embodiment, a sensor interface chip 202 (e.g., a Motorola MC145017) receives an output voltage from the sensing electrode 28 and outputs an analog voltage corresponding to the mass concentration of particles in the ionization chamber 12. The chip 202 is electrically connected to a visual display 44 (e.g., an LCD display) via amplifiers 204, 206.

The monitor 10 desirably is configured to provide a user with a real-time, continuous measurement of the mass concentration of sub-micrometer particles in the surrounding environment. This allows the user to continuously verify that the concentration of such particles is at a safe level.

In addition, the presence of larger dusts does not interfere with the ability of the monitor 10 to measure mass concentrations of sub-micrometer particles because the ionization chamber 12 does not respond to the presence of larger respirable dusts. Thus, the monitor 10 is suitable for use in an environment containing both sub-micrometer particles and respirable dusts. One exemplary use of the monitor 10 is for measuring mass concentrations of DPM in a mining environment containing both DPM and respirable dusts.

In a specific embodiment of the ionization chamber 12 of FIG. 2, the ion source 26, which also serves as a positive field electrode, is a 2.0 mm diameter piece of Am241 with an activity of 0.80 $\mu$Ci. The piece of Am241 is face coated with a 2.0 $\mu$m thick Pd foil and positioned at the center of the lower wall 24. The first region 32 is approximately 0.95 cm in diameter and 0.45 cm in height and the second region 34 is approximately 3.25 cm in diameter and 1.45 cm in height.

As noted above, the sensing electrode 28 desirably is positioned in a plane within the chamber that corresponds approximately to the plane of maximum distortion of the potential within the chamber. When operated at 9.0 volts, the potential at this plane is generally in the range of 3.4 to 3.9 volts, a result of distortion of the electric field and potential due to space charge effects. If there were no source in the chamber, a simple electrostatic analysis indicates that the potential at this plane would be about 6.85 volts. The difference, 2.95 to 3.45 volts, represents the dynamic range for the potential at this position.

EXAMPLE #1

DPM Ionization Monitor

The following example illustrates the use of an ionization-type sensor to accurately and realiably measure DPM concentrations in environments containing both DPM and respirable dusts.

The inventors have previously determined that the primary particle diameter for DPM is in the range of about 25 nm, and that these primary particles aggregate to form filaments of irregular shape with a typical radius of gyration $R_G$ in the range of about 450 to 500 nm. In addition, these aggregates were typically composed of about 1500 individual primary particles. See, Litton, C. D., *Fractal Properties of Smoke Produced from Smoldering and Flaming Fires*, Proceedings ASME International Mechanical Engineering Congress and Exposition, Dallas, Tex., HTD Vol. 352, pp. 119–134 (November 1997).

If it is assumed that each primary particle has a density of 1.5 g/cm$^3$, then the mass of one aggregate particle containing 1500 primary particles is on the order of 2×10$^{-14}$ g, and the number of aggregates per cm$^3$ necessary to achieve a mass concentration of 2×10$^{-9}$ g/cm$^3$ (2 mg/m$^3$) is 1×10$^5$. If the number mean particle diameter dG is taken to be twice the radius of gyration, then the product of $d_G$ and the number concentration $n_O$, or $d_G n_O$, is in the range of 9 to 10. Similarly, if it is assumed that an average respirable coal dust particle has a diameter of 4 $\mu$m and a density of 1.35 g/cm$^3$, then the number of particles necessary to produce the same mass concentration is about 50, so that the product $d_G n_O$ is about 0.02. Since the sensitivity of an ion chamber varies directly with $d_G n_O$, this means that an ionization chamber is about 500 times more sensitive to DPM than to respirable coal dust.

To demonstrate the foregoing, the responsivity of a bipolar ionization chamber, such as the ionization chamber 12 of FIG. 2, and a unipolar ionization chamber 50 (shown schematically in FIG. 2A), to different mass concentrations of DPM, respirable coal dusts, and various mixtures of the two were measured.

As illustrated in FIG. 2A, the primary difference between the unipolar ionization chamber 50 of FIG. 2A and the bipolar ionization chamber 12 is that in the unipolar ionization chamber 50, aerosols are flowed through a region 52 of unipolar ions in which the ions acquire charge via diffusion charging. The charged aerosols then flow out of the chamber into a collection electrode 54, which is operable to produce a current that depends upon the average charge per particle and the number concentration of particles.

By continuously measuring the ion current reduction within the unipolar ion region 52, and the charged particle current at the collection electrode 54, it is possible to obtain an estimate of the average diameter and number concentration of the flowing aerosol. For example, the ratio of primary charging current I when an aerosol is present to the initial, steady-state current $I_O$ when no aerosol is present is denoted by the parameter $\eta$, which depends upon the number mean diameter $d_G$ and number concentration $n_O$ via the expression $$\eta = (1/\kappa_O d_G n_O (1-\exp(-\kappa_O d_G n_O)), \quad (1)$$

where $\kappa_O$ is a chamber constant with an empirically determined value of 0.0217 cm$^2$.

For values of $\eta \geq 0.90$, a Taylor series expansion of equation (1) yields $$1\eta = \tfrac{1}{2}\kappa_O d_G n_O. \quad (b\,2)$$

The charged particle current at the collection electrode, amplified and converted to a voltage, $V_C$, depends upon $\eta$, $d_G$, and the flow $Q_O$ via the expression $$V_C = 0.0325 \cdot Q_O \cdot (1-\eta) \cdot ln(1+2.3 \times 10^7 d_G/Q_O), \quad (3)$$

where $Q_O$ is the flow-rate in cm³/s, which is was held constant at 33.3 cm³/s (21 pm) for these examples.

Thus, the number mean diameter, $d_G$, can be obtained from measurements of $V_C$ and $\eta$ and use of equation (3). Equation (2) can then be used to determine the number concentration, $n_O$.

Figure 11:
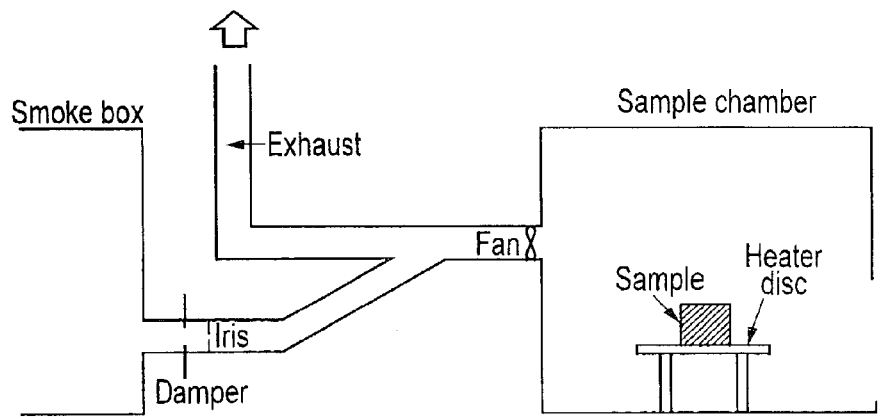
FIG. 11 shows a schematic perspective view and a schematic side view of a dust box, or smoke box, in which experiments were conducted.

In any event, for these examples, as well as other examples described herein, a "dust box" (also referred to herein as a "smoke box") was used, as shown schematically in FIG. 11. In the dust box, dusts and/or aerosols are dispersed near the top of the dust box, allowed to mix thoroughly (if dusts and aerosols are present) and then allowed to fall assisted by gravity and a small, imposed flow. Samples are extracted through 10 mm cyclones near the bottom of the dust box at nominal flow-rates of 21 pm and flowed to various measuring devices. The dust box is described in greater detail in Marple, V. A. and Rubow, K. L., *An Aerosol Chamber for Instrument Evaluation and Calibration*, Am. Ind. Hyg. Assoc. J., Vol. 44, 1983, pp. 361–367, which is incorporated herein by reference. In addition, a Tapered Element Oscillating Microbalance (TEOM) (described above), was used to measure mass concentrations of samples extracted from the dust box.

In one example, DPM, respirable coal dust, and various mixtures of the two were dispersed in the dust box and samples of each were flowed through the unipolar ion chamber 50 to measure the parameter $\eta$ (equation (1)) of each sample. For DPM, the change in $\eta$ was significant, as was expected based on the foregoing theoretical analysis. However, when the ionization chamber 50 was subjected to pure respirable coal dust, there was no discernible change in $\eta$, even for dust concentrations in the range of 11 to 12 mg/m³. Additional measurements were made using various mixtures of DPM and dust. For these measurements, the change in $\eta$ was found to depend only upon the DPM concentration.

In addition, the sensitivity of the ionization chamber 50, expressed as the change in $\eta$ divided by the change in mass concentration of DPM, or $\Delta\eta/\Delta m_{DPM}$, remained constant for pure DPM and for the DPM/dust mixtures. The results of these measurements are shown in FIG. 4A, where the quantity $1-\eta$ is plotted as a function of the DPM mass concentration for pure DPM, pure respirable coal dust, and mixtures of the two. These results confirm that an ionization module, such as the bipolar ionization module 12 of FIG. 2 or the unipolar ionization module 50 of FIG. 2A, can be used for measuring mass concentrations of DPM in atmospheres containing both respirable coal dust and DPM.

Figure 4B:
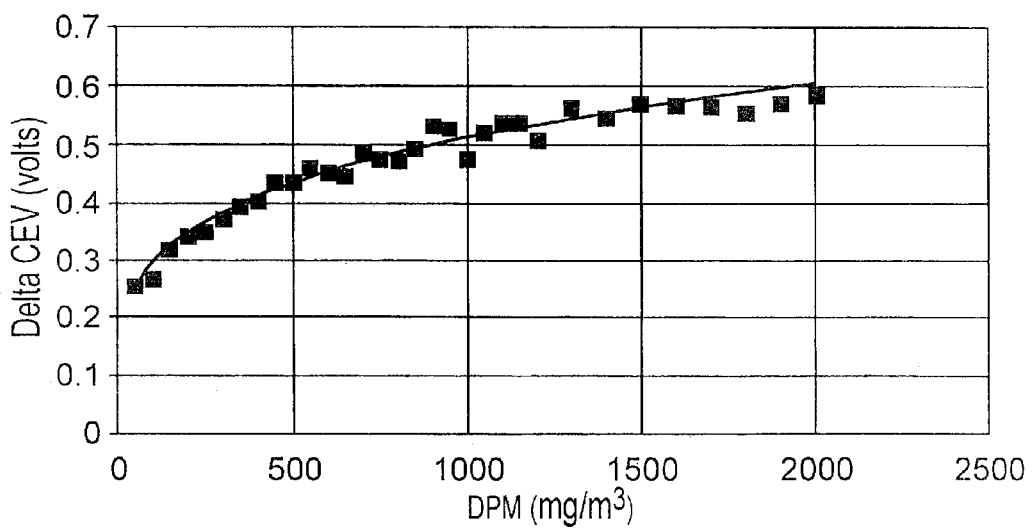
FIG. 4B is a data graph illustrating the measured change in sensing electrode potential, $\Delta$CEV, as a function of DPM mass concentration, using the bipolar ionization chamber of FIG. 2.

In another example, samples of coal dust and DPM were flowed through the bipolar ionization chamber 12 of FIG. 2. For respirable coal dust, there was no response, as previously observed using the unipolar ionization chamber 50. For DPM, the change in potential of the floating, collection electrode increased rapidly at low concentrations ($\leq 0.50$ mg/m³) and then decreased slowly as the DPM mass concentration increased further. FIG. 4B is a plot of the change in the collection (sensing) electrode voltage (CEV) of the ionization chamber as a function of the mass concentration of DPM, spanning the range from zero to 2.0 mg/m³. Throughout the mass range, the following empirical expression (solid curve of FIG. 4B) was found to adequately describe $\Delta$CEV as a function of DPM mass concentration:

$$\Delta CEV = 0.51(m_{DPM})^{0.242} \quad (4)$$

Of particular interest is the concentration range from 50 to 200 µg/m³, since this is the range over which DPM measurements is required in typical applications. Within this range, the empirical expression, defined by equation (4), predicts the measured values to within +/−5%. To demonstrate the utility of this expression, equation (4) is rearranged as $$m_{DPM} = (\Delta CEV/0.51)^{4.1322} \quad (5)$$

so that the predicted mass of DPM can be determined from the measured CEV.

However, the accuracy with which a determination of the DPM mass concentration can be made depends, in part, upon the signal to noise ratio (SNR) of the ion chamber. To address this potential problem, the steady-state CEV was monitored for extended periods of time and measurements made once every two seconds.

These data were then averaged over discrete time intervals up to 120 sec (60 measurements) to determine if time averaging could reduce the electronic noise of the ion chamber. For a total time period of 60 minutes (3600 sec, or 1800 measurements), the average steady-state CEV was 3.416 with a standard deviation of +/−0.015726 volts. From equation (4), at a mass concentration of 100 µg/m³, the change in CEV is 0.292126 volts. At one standard deviation lower, 0.2764 volts, the calculated mass concentration would be 79.6 µg/m³, while at one standard deviation higher, 0.307852 volts, the calculated mass concentration would be 124.2 g/m³. If the measurements are averaged over a time interval of 60 seconds, then the standard deviation is reduced to +/−0.003378 volts. Using this value as the uncertainty in the measurement, the lower and upper calculated mass concentrations would be 95.3 and 104.9 µg/m³, respectively. The use of signal averaging reduces the uncertainty in the mass determination from +/−24% to +/−5%.

Light-Scattering Sensors

Figure 5:
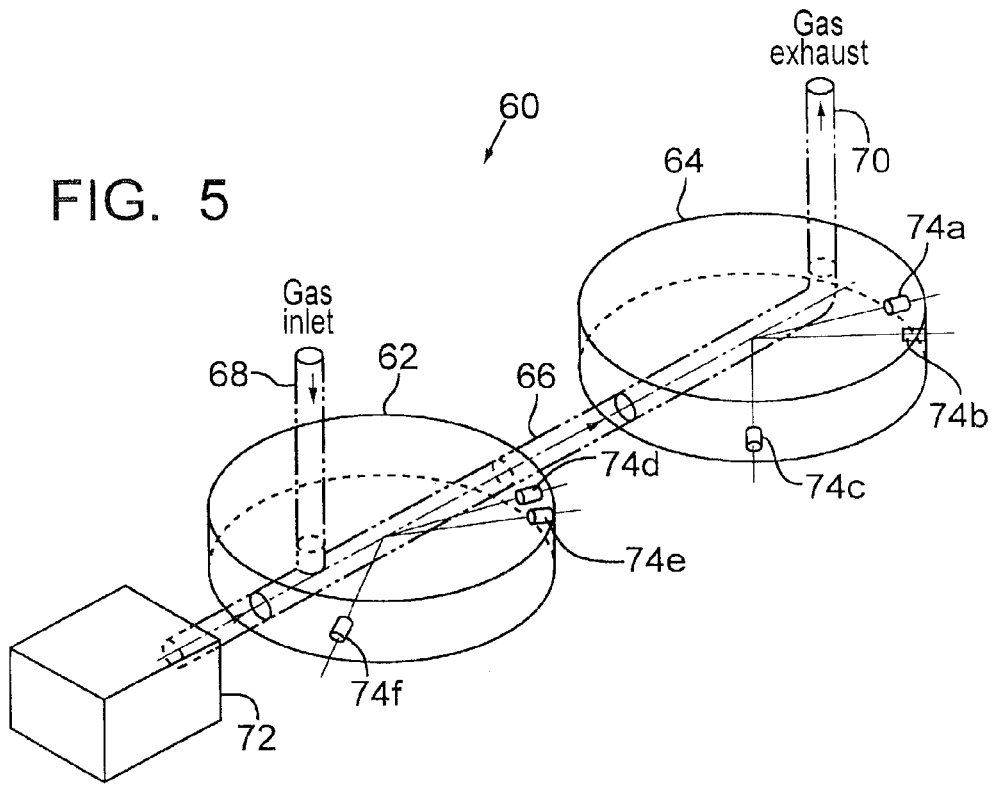
FIG. 5 is a schematic, perspective view of a dual-chamber, light-scattering module according to one embodiment.

Referring to FIG. 5, there is shown a schematic of a dual-chamber light-scattering sensor or module 60, according to one embodiment, which could be implemented in a particle-detecting monitor or in a smoke detector. The light-scattering module 60 also can be used in determining light-scattering properties of different aerosols, as described in the examples below.

The light-scattering module 60 includes a first chamber 62 and a second chamber 64 in fluid communication with each other via a conduit 66. The first chamber 62 includes an inlet conduit 68 and the second chamber 64 includes an outlet conduit 70. Thus, as shown, a flow path is established between the inlet conduit 68, the first chamber 62, the conduit 66, the second chamber 64 and the outlet conduit 70. A light source 72 is positioned to project a light beam into the first and second chambers 62, 64, respectively, along the flow path. A plurality of sensors 74a, 74b, and 74c are positioned to detect scattered light at predetermined angles in the second chamber 64 and a plurality of sensors 74d, 74e, and 74f are positioned to detect scattered light at predetermined angles in the first chamber 62.

In one implementation of the light-scattering module 60, the light source 72 is a small HeNe laser operable at a wavelength of 632.8 nm with an output power level of 3 milliwatts and a beam diameter of 1.0 mm. The first and second chambers 62, 64, respectively, are each 10.16 cm in diameter and 2.54 cm in height and have a center-to-center spacing of 15.2 cm. The air space between the sensors and the central scattering volume of each chamber is cylindrical in shape with a diameter of 0.25 cm. Each sensor is a PIN-125DP/L silicon photodiode detectors with measured responsivities of 0.24 A/W at a wavelength of 632.8 nm. The active surface of each sensor is spaced 4.45 cm from the center of their respective chambers 62, 64.

Figure 6:
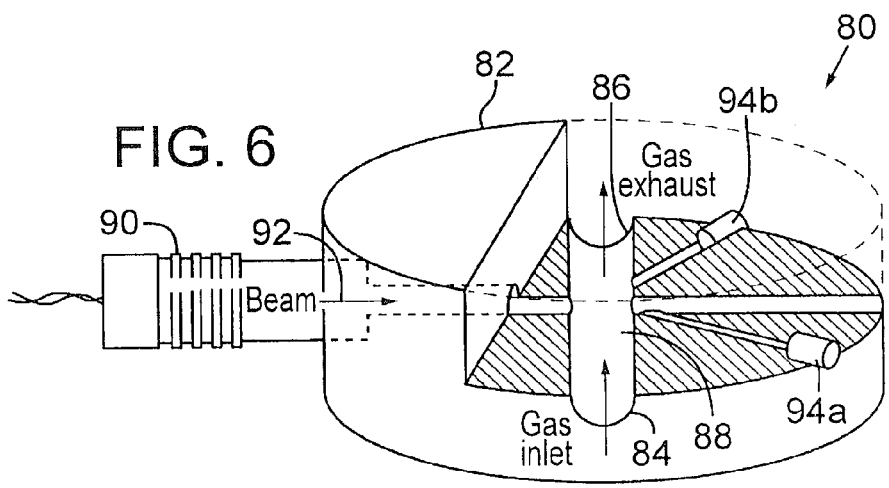
FIG. 6 is a schematic, perspective view of a single-chamber light-scattering module according to one embodiment, shown partially in section.

Referring to FIG. 6, there is shown a schematic of a single-chamber light-scattering sensor or module indicated generally at 80, which could be implemented in a particle-detecting monitor, such as a monitor for measuring mass concentrations of particles in the atmosphere, or in a smoke detector. The light-scattering module 80 also can be used in determining light-scattering properties of different aerosols, as described in the examples below.

The light-scattering module 80 includes a housing or chamber 82, having a generally cylindrical shape. The chamber 82 is formed with an inlet opening 84 and an outlet opening 86 to define a flow path 88 desirably extending through the center of the chamber 82. A light source 90 is positioned to project a light beam 92 in a direction that is substantially perpendicular to the flow path 88. One or more light-detecting sensors 94a and 94b are positioned to detect scattered light at predetermined angles in the chamber 82. Each light-detecting sensor 94a, 94b is operable to provide a respective output signal (e.g., a voltage signal) corresponding to the intensity of scattered light measured by the respective sensor 94a, 94b.

Desirably, the angles at which the light-detecting sensors 94a, 94b detect scattered light are selected such that intensities per unit mass concentrations vary linearly with mass concentrations, and independent of particle size and particle volatility. In this manner, accurate measurements of particle mass concentrations can be obtained. For example, it was found that positioning a light-detecting sensor to measure scattering light at an angle in the range of about 15° to 30° in the forward direction was effective to minimize the effects of particle size and dust volatility.

Suitable control electronics (not shown) may be provided for receiving and further processing of the respective output signals from the light-detecting sensors 94a, 94b. In a particle analyzer for measuring the mass concentration of particles flowing through the chamber 82, for example, the control electronics may be configured to translate an output signal from one of the light-detecting sensors 94a, 94b into the mass concentration of particles flowing through the chamber 82, which may be accomplished, for example, by multiplying the measured angular intensity by an empirically-derived constant.

In alternative embodiments, the light-scattering module 80 can be implemented into a smoke detector for detecting aerosols produced by combustion. As further described in the examples below, the light-scattering module 80 was found to be more sensitive to aerosols produced by smoldering combustion than to aerosols produced by flaming combustion, and more sensitive to aerosols produced by flaming combustion than to DPM. These relative sensitivities can be used to discriminate between combustion aerosols and DPM for detecting the presence of combustion aerosols in atmospheres contaminated by DPM, or even to discriminate between smoldering combustion aerosols and flaming combustion aerosols for determining the particular stage of combustion. Several approaches for discriminating between DPM, smoldering combustion aerosols and flaming combustion aerosols with a light-scattering sensor are discussed in the examples below.

In a working embodiment of the light-scattering module 80, the light source 90 is a small laser diode operable at a wavelength of 635 nm with an output power level of 5 to 6 milliwatts and a beam diameter of 2.0 mm. The chamber 82 is 7.62 cm in diameter and 2.54 cm in height. The air space between the sensors 94a, 94b and the central scattering volume is cylindrical in shape with a diameter of 0.2 cm. Each sensor is a PIN-125DP/L silicon photodiode detectors with measured responsivities of 0.39 A/W at a wavelength of 635 nm. The active surface of each sensor is spaced 3.2 cm from the center of the chamber 82.

For both light-scattering modules 60 and 80, the actual scattering volumes vary inversely with the sine of the scattering angle, so that as the angle increases, the scattering volume decreases. Assuming the scattering volumes to be defined by the light source beam diameters, $d_{BEAM}$, and the diameters of the cylindrical light paths from the beam to the detectors, $d_{DET}$, then the volumes at each angle may be calculated approximately from the expression:

$$V(\theta) = (\pi/4) d_{DET}^2 d_{BEAM} / \sin(\theta). \tag{6}$$

Dual Light-Scattering and Ionization Module

Figure 7:
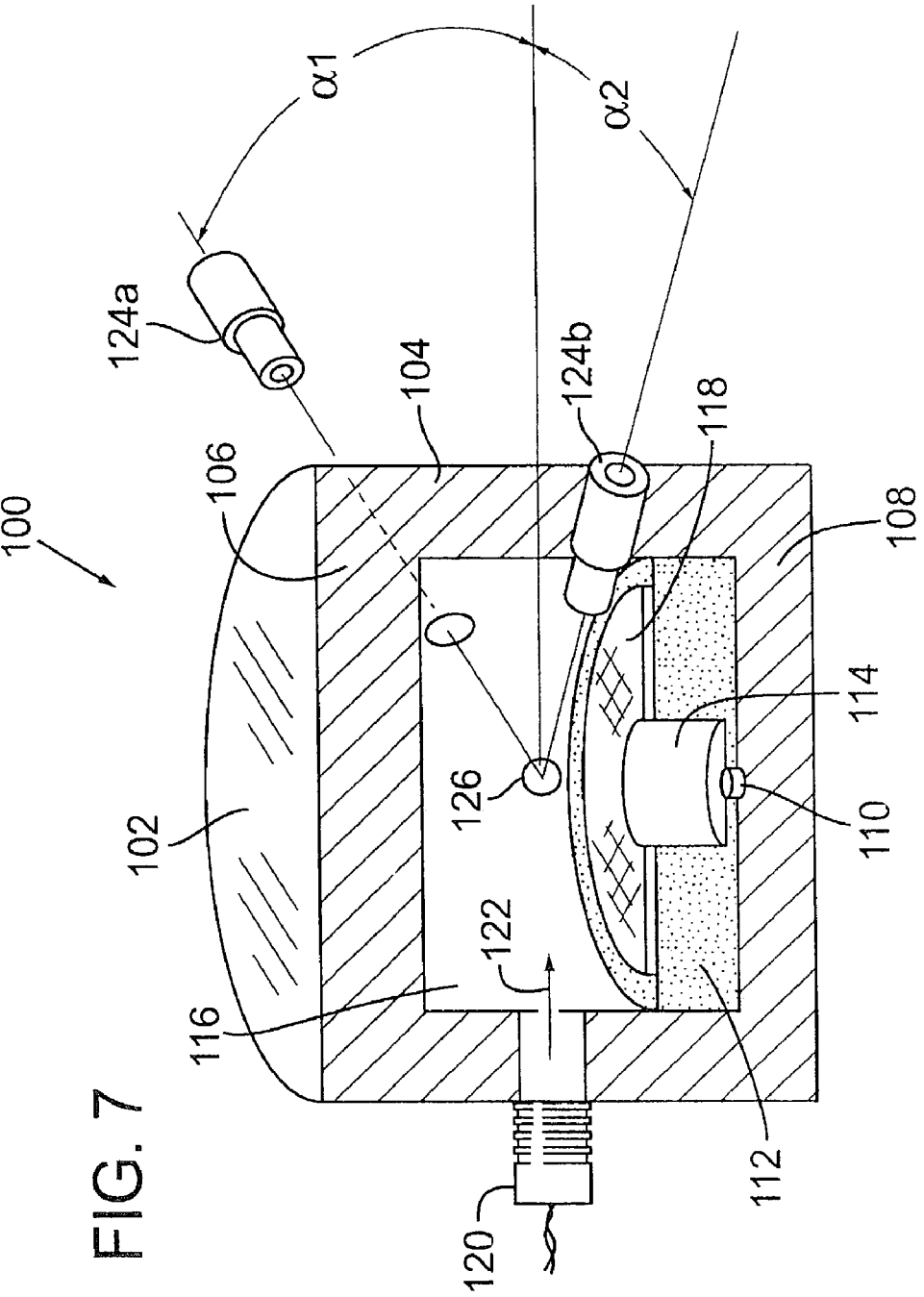
FIG. 7 is a schematic, perspective view of a dual light-scattering and ionization module according to one embodiment, shown partially in section.

FIG. 7 illustrates a schematic a dual light-scattering and ionization module, indicated generally at 100, according to one embodiment, which essentially is a combination of the ionization module 12 of FIG. 2 and the light-scattering module 80 of FIG. 6. The module 100 could be implemented in a particle monitor for providing continuous, simultaneous, and independent measurement of both respirable dust and sub-micrometer particles, such as DPM, in environments such as underground mines where both types of particles are present. Alternatively, the module 100 could be implemented in a smoke detector for accurately detecting aerosols produced by flaming or smoldering combustion in atmospheres contaminated by background emissions such as DPM.

As shown in FIG. 7, the module 100 includes a housing, or chamber, 102, which is generally cylindrical in shape having a cylindrical side wall 104 bounded by an upper wall 106 and a lower wall 108. The chamber 102 serves as both an ionization chamber and a light-scattering chamber. The particular shape of the chamber 102, however, is not limited to that of the illustrated embodiment. Accordingly, the chamber 102 may be any of various other geometric shapes.

An ion source 110, such as Am241, positioned on the inner surface of the lower wall 108, serves as a source of ions and as a first field electrode for the chamber 102. The upper wall 106 in the illustrated embodiment is made from metal, and thus serves as a second field electrode for the chamber 102. An annular-shaped electrical insulator 112 is disposed on the inner surface of the lower wall 108 so as to separate the interior of the chamber 102 into a first cylindrical-shaped region 114 and a second, larger cylindrical-shaped region 116. A sensing electrode 118 is disposed on the top surface of the insulator 112 for measuring the electric potential in the chamber 102. Desirably, the sensing electrode 118 is positioned in a plane that corresponds approximately to the plane of maximum distortion of potential within the chamber 102.

A suitable light source 120, such as a diode laser, is supported by the side wall 104 and is positioned to project a light beam 122 through the chamber 102 in a horizontal plane between the upper wall 106 and the sensing electrode 118. One or more light-detecting sensors 124a and 124b also are supported by the side wall 104 and are positioned to detect scattered light at predetermined angles α1 and α2, respectively, within the chamber 102. Desirably, the angles α1 and α2 are selected such that intensities per unit mass concentrations vary linearly with mass concentrations, and independent of the particle size and volatility.

The chamber 102 is formed with an inlet opening 126 and an outlet opening (not shown) positioned at generally diametrically opposing sides of the side wall 104 (such as shown in FIGS. 2 and 6) such that a flow path extends through the chamber 102 in a direction that is generally perpendicular to the light beam 122. A pump (not shown) or another equivalent device may provided for inducing a flow of particulate matter through the chamber 102 from the inlet opening 126 to the outlet opening (not shown).

The configuration of module 100 is not limited to that of the illustrated embodiment. For example, the chamber 102 may be an open-type chamber, such as used in conventional smoke detectors, having a plurality of apertures or windows formed in the side wall 104 to permit gas to freely flow into the chamber, such as via diffusion or convective air flows. In this configuration, a pump would be optional.

In addition, dual light-scattering and ionization modules other than the illustrated single-chamber module are possible. In one configuration, for example, a dual light-scattering and ionization module includes the ionization module 12 of FIG. 2 and the light-scattering module 80 of FIG. 6 in fluid communication with each other (e.g., a conduit extending from the outlet 16 of the ionization module 12 to the inlet 84 of the light-scattering module 80). Alternatively, the dual-chamber light-scattering module 60 of FIG. 5 may be used in lieu of the single-chamber light-scattering module 80 in the latter configuration.

In any event, the sensing electrode 118 and the light-detecting sensors 124a, 124b may be electrically coupled to suitable control electronics (not shown) for simultaneously and independently measuring mass concentrations of both respirable dust and sub-micrometer particles in the chamber 102.

In one specific approach, this is accomplished by optically measuring the total particle mass concentration (including respirable dusts and sub-micrometer particles) using the light-scattering portion of the module 100 (i.e., the light source 120 and light-detecting sensors 124a, 124b). This involves measuring the angular intensity of scattered light with one of the sensors 124a, 124b. Thereafter, the angular intensity is translated by the control electronics into the total particulate mass concentrations, for example, by multiplying the angular intensity by an empirically-derived constant.

As discussed above, the ionization module 12 of FIG. 2 is operable to sense sub-micrometer particle concentrations, while remaining substantially insensitive to larger respirable dusts. Similarly, the ionization portion of the dual module 100 (i.e., ion source 110, sensing electrode 118 and field electrode 106) is used to measure the sub-micrometer particle concentration in the chamber 102. Thus, the mass concentration of respirable dust in the chamber 102 can be obtained by subtracting the ionization-measured sub-micrometer particle mass concentration from the optically-measured total mass particle concentration.

The dual module 100 and the control electronics (not shown), along with a suitable display unit (e.g., an LCD display), may be packaged in housing (such as shown in FIG. 1) to provide an integral particle-measuring monitor. Such a monitor may be worn or carried by a user, such as a mine worker, for continuous monitoring of particle mass concentrations in the surrounding environment. By way of example, one exemplary application of the monitor would be for continuous monitoring of both DPM mass concentrations and respirable coal dust concentrations in a mining environment. Another application is the monitoring of quartz or silica dusts, responsible for silicosis, in atmospheres contaminated by DPM.

In addition to its use as a monitor for measuring particle mass concentrations, the dual chamber module 100 could be implemented in a smoke detector for accurately detecting aerosols produced by combustion in the presence of background emissions such as DPM. As described in the examples below, ionization-type sensors were found to be more sensitive to DPM than to aerosols from flaming combustion, and more sensitive to aerosols from flaming combustion than to aerosols from smoldering combustion. On the other hand, light-scattering sensitivities are in the reverse order; that is, light-scattering sensors were found to be less sensitive to DPM than to aerosols from flaming combustion, and less sensitive to aerosols from flaming combustion than to aerosols from smoldering combustion.

Accordingly, these relative sensitivities can be utilized to discriminate between DPM and combustion aerosols and/or between flaming combustion aerosols and smoldering combustion aerosols. In one specific detection process, the response of an ionization sensor (CEV) and the response of a light-scattering sensor (I) are measured. The measured responses can be compared to each other, and a determination can be made as to whether the responses are indicative of the presence of combustion aerosols or merely DPM in the atmosphere. If the response of the light-scattering sensor is sufficiently greater than the response of the ionization sensor, indicating that combustion aerosols are present, an alarm may be activated.

In one approach for determining when an alarm condition is reached, the ratio of the response of the ionization sensor to the response of the light-scattering sensor (CEV/I) is compared to a predetermined alarm value. If this ratio is less than the predetermined value, indicating that combustion aerosols are present, an alarm may be activated. In an alternative approach, the ratio of the response of the light-scattering sensor to the response of the ionization sensor (I/CEV) is compared to a predetermined value, and an alarm is activated if the ratio exceeds the predetermined value. Other methods for discriminating between DPM and combustion aerosols and/or between flaming combustion aerosols and smoldering combustion aerosols are described in the examples below.

EXAMPLE #2

Respirable Coal Dust

This example illustrates how to determine optimum scattering angles for measuring respirable coal dust concentrations with a light-scattering module (e.g., the module 60 of FIG. 5, the module 80 of FIG. 6, or the dual module 100 of FIG. 7).

The chemical composition of various coals varies dramatically from anthracite coal, which contains mostly carbon and a low volatility in the range of 4%, to a form of coal called gilsonite, which contains less carbon and a volatility in the range of 85%. The index of refraction, $m=n-ik$, and in particular the extinction coefficient k, is a strong function of both coal volatility and wavelength of incident radiation. For instance, for coal with a volatility of 5%, the value of k at a wavelength of 632.8 nm is about 0.41, while for coal with a volatility of 40%, k has a value of about 0.05. If the wavelength is increased to 900 nm, the corresponding respective values decrease to 0.18 and 0.02. The real component n tends to vary slightly with coal volatility, but the variation with wavelength is negligible throughout the visible and near-infrared regions of the spectrum.

Figure 8:
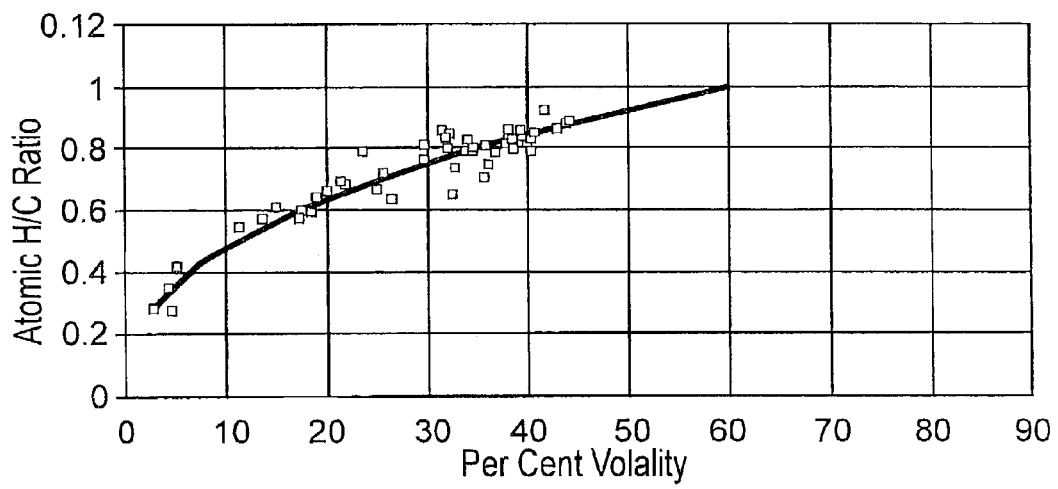
FIG. 8 is a data graph illustrating the dependence of Atomic H/C ratio on the percent volatility of different respirable coal dusts.

Generally, available data for n and k are given in terms of the atomic hydrogen to carbon ratio, H/C, and it is necessary to convert measured values of coal volatility to H/C values. FIG. 8 is a plot of the atomic H/C ratio as a function of the percent volatility for a wide range of coals. The data shown in FIG. 8 were obtained from Cannon, C. G. and George, H. W., Proceedings of a Conference on the Ultra-Fine Structure of Coals and Cokes,. London, England, pp. 290–316 (1943), and from proximate and ultimate analyses of different coals obtained over the years. A linear regression of these data yields the following empirical expression for H/C as a function of volatility:

$$H/C = 1.23 \, (\% \text{ volatility}/100)^{0.4125} \quad (7)$$

The variation of k with the ratio, H/C, and with $\lambda$ is found to follow the empirical expression $$k = k_O \cdot e^{3\lambda}, \quad (8)$$

where $\lambda$ is the wavelength of incident light in $\mu$m, and $$k_O = 5.35 - 7.25(H/C) \text{ for } H/C \leq 0.60, \text{ or}$$

$$k_O = 15 \cdot e^{-4.5}(H/C) \text{ for } H/C > 0.60.$$

Figure 9:
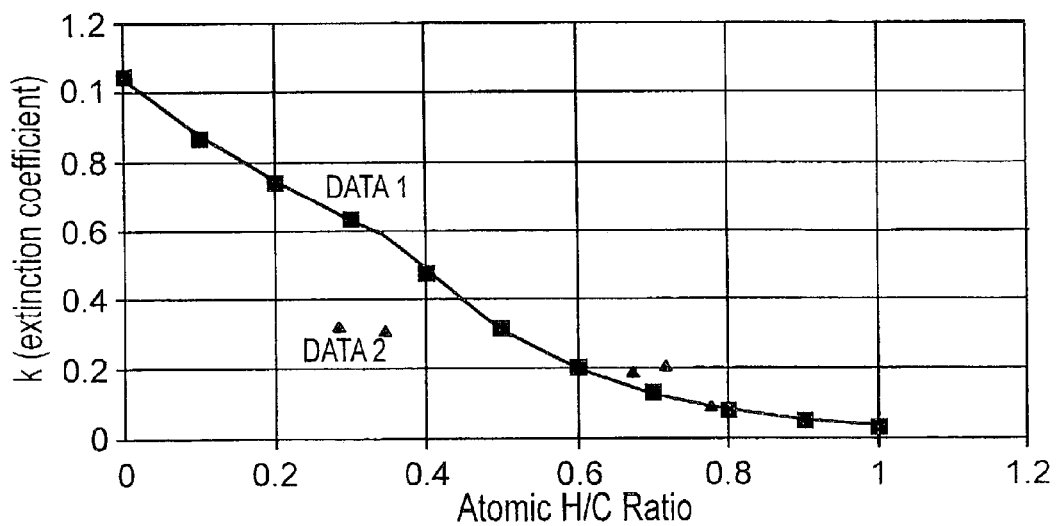
FIG. 9 is a data graph of the extinction coefficient, k, (imaginary component of the complex index of refraction) as a function of the Atomic H/C ratio.

FIG. 9 is a plot of k v. the atomic H/C ratio at a wavelength of 546 nm (0.546 $\mu$m) generated using the above expressions and available data from Cannon, et al. and McCartney, J. T. and Ergun, S., *Optical Properties of Coals and Graphite*, U.S. Bureau of Mines Bulletin 641, (1967). An additional analysis of the data from these references indicates that n depends upon the H/C ratio via the expression $$n = 2.17 - 0.51(H/C). \quad (9)$$

The use of these expressions then allows for the determination of the index of refraction, m, for any coal, from a simple measurement of the coal volatility. These expressions were then incorporated into a robust Mie scattering algorithm, such as described in Barber, P. W. and Hill, S. C., *Light Scattering by Particles: Computational Methods*, World Scientific Publishing Co. Pte. Ltd., (990), so that the effects of volatility on the angular intensity distribution of scattered light could be determined.

In addition to the effects of coal volatility, the algorithm was modified to obtain the integral average angular intensities over a distribution of particle sizes. For these examples, the size distribution was assumed to be lognormal, and different distributions were input into the algorithm by specifying the mass mean diameter $d_M$ and the geometric standard deviation of the distribution $\sigma$. In addition to size distribution parameters and coal volatility, other inputs included the wavelength of incident radiation $\lambda$ and the angular increment $\Delta\theta$, which could be varied in increments of 1°, 3°, 5°, and up to increments of 90° so long as increments in excess of 5° are divisible by 5.

Over the years, several field investigations to determine respirable dust particle size distributions in underground coal mines were conducted. Three extensive surveys are summarized in Marple, V. A., D. B. Kittelson, K. L. Rubow and C. P. Fang, *Methods for the Selective Sampling of Diesel Particulate in Mine Dust Aerosols*, Final Report, Contract J0145022, University of Minnesota, (October 1986), in which approximately 110 different distributions are tabulated, encompassing several mines, as well as different locations within mines. Within these data, values of $d_M$ vary over the range of 2.7 to 10 $\mu$m (average about 6.0 $\mu$m) while values of $\sigma$ vary over the range of 1.7 to 3.2 (average about 2.35). Most of the data contain little information on the volatility of the coal, but from the names of the mines and coal seams listed, the coal volatility could be estimated to lie in the range of 15% to 40%. These data indicate the diversity of respirable dust particle size distributions that can exist within underground mines.

Figure 10:
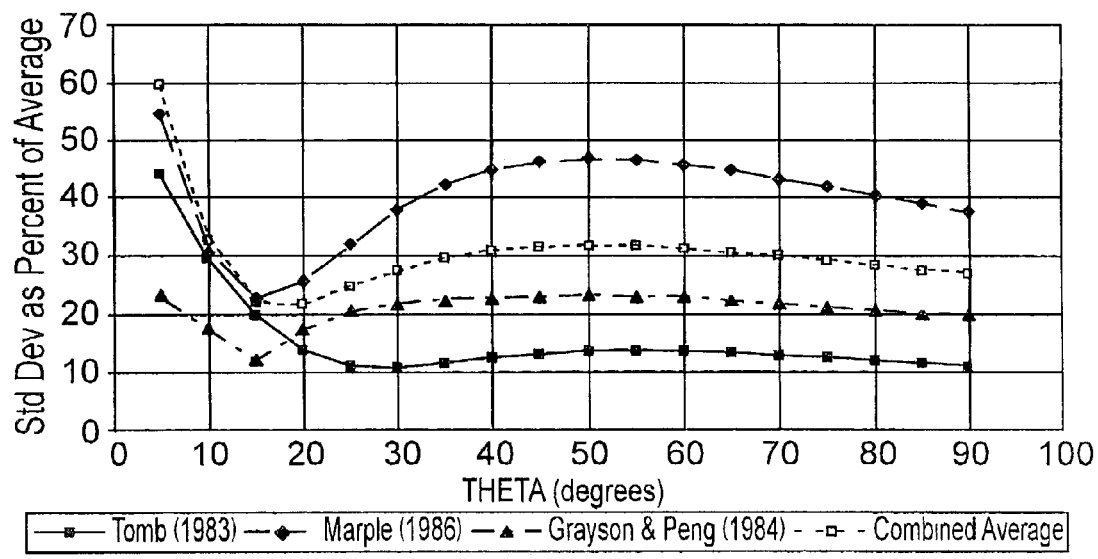
FIG. 10 is a data graph of the standard deviation, expressed as a percent of the mean intensity, as a function of scattering angle for respirable coal dust size distributions, using $\lambda$= 632.8 nm and averaged over the range of volatilities from 15% to 45%.

As should be expected, when the angular intensities are calculated individually, using the Mie scattering algorithm, for these size distributions at a fixed volatility and wavelength, differences result. To assess the magnitude of these differences, the arithmetic means and standard deviations of the calculated intensities at angles from 5° to 90°, in increments of 5°, at an average volatility of 30% and a wavelength of 632.8 nm were computed and the standard deviation then expressed as a percentage of the arithmetic mean. The results for each data set, and for the three data sets combined, are shown in FIG. 10. Differences exist between the different data sets, but all three, along with the combined average show that the angular region corresponding to the minimum variation lies in the range of 15° to 30°. It should be noted that FIG. 10 does not address any effects due to volatility.

In this example, two types of coal dusts with identical size distributions, but with volatilities of 36.1% and 17.2%, were dispersed in the dust box and angular intensities of each dust were measured using the light-scattering module 60 of FIG. 5. The light-detecting sensors 74a, 74b, 74d, 74e of the light-scattering module 60 were positioned to measure scattered light at 22½°, 45°, 15°, and 30°, respectively, in the forward direction.

Figure 12A:
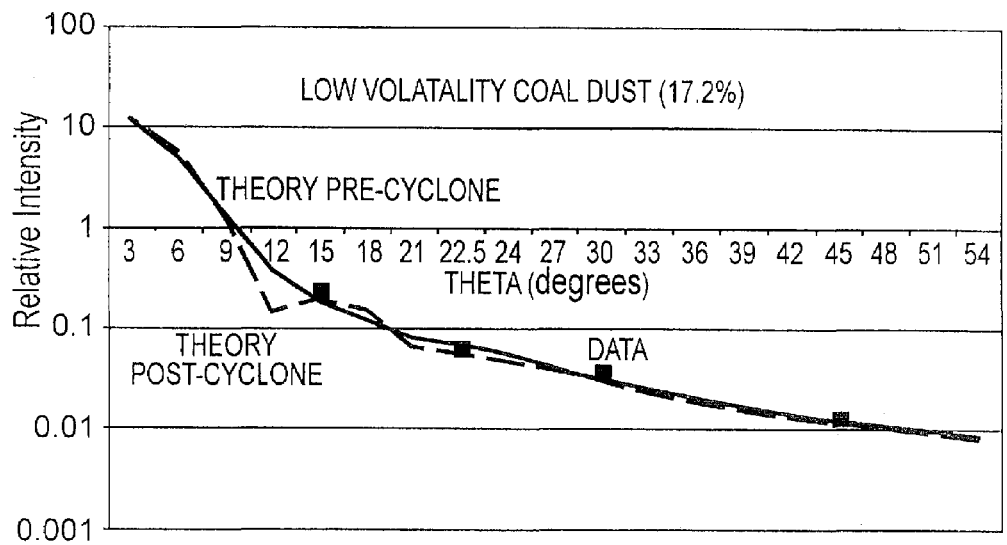
FIGS. 12A and 12B are data graphs of measured and predicted angular intensities for two coals of uniform particle size distribution, but differing in volatility by more than a factor of 2.
Figure 12B:
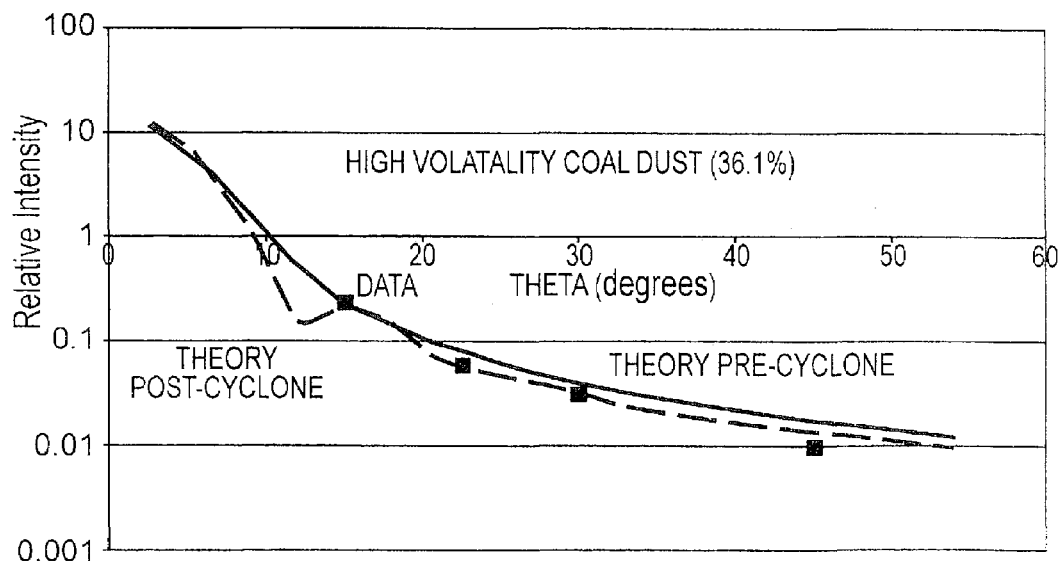

The angular intensity distributions for the two coal dusts were measured, normalized to the value at 15°, and then compared to the data. The results for the low volatility coal dust (17.2%) and the high volatility coal dust (36.1%) are shown in FIGS. 12A and 12B, respectively. For each of the dusts, there are shown two theoretical curves. One curve corresponds to the dust particle size distribution without passage through the 10 mm cyclone and the other curve corresponds to the calculated size distribution after passage through the 10 mm cyclone. The net effect of passage through the cyclone is to reduce the number of larger particles that pass through the cyclone more drastically than the smaller particles, thus resulting in a smaller mass mean diameter and a much narrower distribution. For the as received dusts, the measured distributions had a mass mean diameter of 5.7 $\mu$m and a $\sigma$ of 1.45. After passage through the cyclone, the mass mean diameter was calculated to be 3.75 $\mu$m with a $\sigma$ equal to 1.15. The theoretical intensity distributions were then calculated for each of these distributions. The agreement between the theory and the experiment are very good, in spite of the fact that the theoretical computation assumes perfectly spherical particles, when, in reality, dust particles have quite irregular shapes.

Subsequently, mass concentrations and intensities of dusts of unknown size distribution and volatility were measured. These measurements, obtained for respirable coal dust concentrations in the range of 1 to 12 mg/m³, showed that the intensities per unit mass are constant at both 15° and 22½°, but at 30° and 45° the intensities per unit mass begin to differ, and at 45° this difference is in the range of 20 to 30%. These measurements are in excellent agreement with the results predicted from the theoretical analysis, where at a wavelength λ=600 nm, the optimum angle for measurement was found to lie in the range of 15° to 30°.

EXAMPLE #3

DPM and Respirable Coal Dust

This example illustrates how a light-scattering sensor can be used to identify a particular type of aerosol. In the presentation of data set forth below, all measurements made using the light-scattering module 60 of FIG. 5 are denoted with the subscript "1," while all measurements made using the light-scattering module 80 of FIG. 6 are denoted with the subscript "2."

In this example, DPM, respirable coal dust, and mixtures of the two in concentrations of 2 to 8 mg/m$^3$, 6 to 11 mg/m$^3$, and 11 to 13 mg/m$^3$, respectively, were flowed through the light-scattering module 60 and angular intensities were measured at 15°, 22½°, 30°, and 45° in the forward direction.

In general, the measurements show that the intensities per unit mass for DPM were lower than those for respirable coal. FIG. 13 is a plot of the average intensities measured at 15° for pure DPM, pure respirable coal dust, and mixtures of the two. For pure DPM the average intensity per unit mass is in the range of 0.022 volts/(mg/m$^3$), while for pure respirable coal dust the intensity per unit mass is around 0.065 volts/(mg/m$^3$). Perhaps of greater significance are the angular intensity ratios for the two types of particles. These ratios are shown in Table 1 below, where the number in parentheses is the angle at which the measurement was made. It should be noted that these ratios are averages of the raw data, uncorrected for differences in the angular scattering volumes.

TABLE 1

Average angular intensity ratios measured for pure concentrations of DPM and pure concentrations of respirable coal dust.

| RATIO | DPM | DUST |
|---|---|---|
| $I_1(15)/I_1(22)$ | 2.36 | 3.14 |
| $I_1(15)/I_1(30)$ | 6.45 | 11.82 |
| $I_1(15)/I_1(45)$ | 13.76 | 37.90 |

These data show that the intensity for respirable coal dust decreases rapidly as the angle increases, while for DPM the intensity decrease is more gradual. These ratios were also measured for mixtures of DPM and respirable coal dust and the resulting ratios $I_1(15)/I_1(30)$ and $I_1(15)/I_1(45)$ were found to decrease linearly as the mass fraction of DPM increased from 0 to 1. These results, as shown in FIG. 14, show that when DPM/dust mixtures exist, a determination of one of these ratios could be used to estimate the relative mass fractions of the two components.

However, considering that the allowable time weighted average concentration of DPM is a factor of 10 lower than that for dust, this determination may have limited applicability, especially in mixtures where DPM is ≦about 10% of the total mixture. Nonetheless, determination of one of these ratios could be used as a check of some other measurement or combination of measurements, and/or to increase the reliability of the data or the inferred mass measurements.

In another example, samples of respirable dust at mass concentration in the range of about 1.0 to 4.5 mg/m$^3$ were flowed through the light-scattering module 80 of FIG. 6 and angular intensities were measured at 15° and 30° in the forward direction. The average sensitivity at 15°, expressed as the change in intensity divided by the change in respirable dust mass concentration, $\Delta I_2(15)/\Delta m_{DUST}$, was 0.113 volts/(mg/m$^3$)+/−22%. The average sensitivity at 30°, $\Delta I_2(30)/\Delta m_{DUST}$, was 0.032 volts/(mg/m$^3$)+/−16%. These values are significantly higher than those previously obtained using the light-scattering module 60 of FIG. 5, which provided sensitivities of $\Delta I_1(15)/\Delta m_{DUST}$=0.065 and $\Delta I_1(30)/\Delta m_{DUST}$=0.0055 at 15° and 30°, respectively.

Next, samples of DPM at concentrations of about 0 to about 3.0 mg/m$^3$ were flowed through the light-scattering module 80 and angular intensities were measured at 15° and 300 in the forward direction. The average sensitivities for angular scattering at 15° and 30° were measured to be $\Delta I_2(15)/\Delta m_{DPM}$=0.064 volts/(mg/m$^3$)+/−10.5% and $\Delta I_2(30)/\Delta m_{DPM}$=0.0314+/−11.2%, respectively.

The difference in sensitivities at 15° and 30° for DPM is 0.0326 volts(mg/m$^3$), while the difference in sensitivities 15° and 30° for respirable coal dust is 0.081 volts/(mg/m$^3$), a factor of 2.5 greater. The difference in sensitivities at the two angles (i.e., the slope) is sufficiently different to allow for a determination of whether the particles in the light-scattering module 80 are DPM or respirable coal dust.

EXAMPLE #4

DPM and Combustion Aerosols

This example illustrates the use of an ionization sensor and/or a light-scattering sensor to detect combustion aerosols in atmospheres contaminated with DPM.

It is known that ionization-type smoke detectors are more sensitive to aerosols produced from flaming combustion than they are to aerosols produced from smoldering combustion. The reason for this difference in sensitivity is the result of two factors. First, the response of an ionization chamber to the presence of an aerosol at low concentrations varies directly with the product of number mean particle diameter, $d_G$, and number concentration no, or $d_G n_O$. Consequently, for aerosol sources that produce large numbers of very small particles, the sensitivity will be high. Second, when small particles form aggregates of much larger extent, high sensitivity also will result for low to moderate concentrations of these larger aggregates.

The inventors have previously determined that the primary particle diameters for flaming and smoldering combustion aerosols are around 30 and 70 nm, respectively. Flaming combustion aerosols form aggregate particles containing 500 to 1000 of the primary particles (an average mass of around 1.5×10$^{-14}$ g) having an average radius of gyration $R_G$ in the range of 350 to 400 nm. Smoldering combustion aerosols tend to form aggregates containing roughly 100 primary particles (an average mass of around 2.5×10$^{-14}$ g) having an average $R_G$ in the range of 200 to 250 nm. See, Litton, C. D., *Fractal Properties of Smoke Produced from Smoldering and Flaming Fires*, Proceedings ASME International Mechanical Engineering Congress and Exposition, Dallas, Tex., HTD Vol. 352, pp. 119–134 (November 1997).

At an average mass concentration of 2×10$^{-9}$ g/cm$^3$ (2 mg/m$^3$) the number of flaming aggregates per cm$^3$ no is around 1.3×10$^5$ while the number of smoldering aggregates is about 8 5×10$^4$. If $d_G$ is set equal to $2R_G$, then for flaming aggregates $d_G n_O$ is in the range of 4.5 to 5, while for smoldering aggregates the value is in the range of 1.6 to 2.0. These calculations show that an ion chamber is 2 to 3 times more sensitive to flaming combustion aerosols than to smoldering combustion aerosols. If it were assumed that no aggregation occurred, then the difference in sensitivities would be even greater.

The inventors also have previously determined that the primary particle diameter for DPM is in the range of 25 nm and that these primary particles aggregate to form filaments of irregular shape with a typical radius of gyration $R_G$ in the range of 45° to 500 nm. In addition, these aggregates are typically composed of about 1500 individual primary particles.

If it is assumed that each primary particle has a density of 1.5 g/cm$^3$, then the mass of one aggregate particle containing 1500 primary particles is on the order of $2 \times 10^{-14}$ g, and the number of aggregates per cm$^3$ necessary to achieve a mass concentration of $2 \times 10^{-9}$ g/cm$^3$ (2 mg/m$^3$) is $1 \times 10^5$. If the number mean particle diameter is taken to be twice the radius of gyration, then the product $d_G n_O$ is in the range of 9 to 10. This calculation shows that an ion chamber is about 2 to 3 times more sensitive to DPM than to aerosols from flaming combustion and about 5 to 6 times more sensitive to DPM than to aerosols from smoldering combustion.

Regardless of the exact relative values, these numbers show that an ion chamber is significantly more sensitive to DPM than to aerosols produced from either flaming or smoldering combustion while light scattering sensitivities are in the reverse order. Thus, if the ratio of ion chamber response to light scattering response were obtained for the different types of aerosols, then a high value would result for DPM, a lower value for flaming combustion aerosols, and a much lower value for smoldering combustion aerosols. Consequently, this ratio could be used to provide for a high degree of discrimination between the different types of aerosols in a fire sensor having both an ionization chamber and a light-scattering module.

In this example, the response of the bipolar ionization chamber 12 and angular intensities in the light-scattering module 80 were measured for DPM, flaming combustion aerosols (FCA), smoldering combustion aerosols (SCA), and mixtures of DPM/FCA and DPM/SCA. The dust box shown in FIG. 11 was used to generate FCA, SCA, and mixtures of DPM/FCA and DPM/SCA.

The DPM and combustion aerosol mass concentrations in this example varied over a broad range, from roughly zero to more than 50 or 60 mg/m$^3$, although in the data and analysis that follow particular attention was paid to mass concentrations <10 mg/m$^3$, since this is the region that early-warning fire detection is generally achieved. The basic data acquired are summarized as averages in the Tables 2, 3, and 4 below, in which the averages represent measurements from 2 to 4 tests for each aerosol source. It is also worth noting that although differences occurred between sources, these differences were generally within +/−15−20% of the average reported. Also, the sensitivities, presented in terms of the signal per unit mass concentration, were determined from linear regressions of the signals as functions of the mass concentrations. This approach is preferable to simple signals divided by the mass concentrations because it better reflects the changes in signal per unit change in mass concentrations.

TABLE 2

Measured sensitivities, volts/(mg/m$^3$), for diesel exhaust particles and various combustion aerosols using the bipolar ionization chamber 12 with floating collection electrode and the light-scattering module 80.

| Aerosol Source | ΔCEV/M | ΔI(15)/M | ΔI(30)/M | ΔI(15)/M−ΔI(30)/M |
|---|---|---|---|---|
| Diesel Exhaust Flaming | 0.2083 | 0.0122 | 0.007 | 0.0052 |
| No. 2 Diesel Fuel | 0.0529 | 0.0884 | 0.0372 | 0.0512 |
| Pgh Seam Coal | 0.0457 | 0.0733 | 0.0360 | 0.0373 |
| SBR | 0.0684 | 0.0977 | 0.0399 | 0.0578 |
| Douglas Fir | 0.1082 | 0.0755 | 0.0403 | 0.0352 |
| Bond Paper | 0.1255 | 0.0659 | 0.0263 | 0.0396 |
| Smoldering | | | | |
| Pgh Seam Coal | 0.0280 | 0.1450 | 0.0760 | 0.0690 |
| SBR | 0.0252 | 0.2140 | 0.0888 | 0.1252 |
| Douglas Fir | 0.0212 | 0.1645 | 0.0722 | 0.0923 |

Table 2 shows that the ionization chamber is most sensitive to DPM, less sensitive to aerosols from flaming combustion, and even less sensitive to aerosols from smoldering combustion. Table 2 also shows that the light-scattering module is most sensitive to aerosols from smoldering combustion, less sensitive to aerosols from flaming combustion, and even less sensitive to DPM.

In addition, these measurements show that the ratios of change in ion chamber CEV to change in angular intensities, ΔCEV/ΔI(15), ΔCEV/ΔI(30), ΔCEV/(ΔI(15)−ΔI(30)), or even the intensity difference ΔI(15)−ΔI(30) may be sufficient to discriminate between particles produced from fires and particles produced from diesel exhausts. The values from Table 2 were computed as averages for the three generic sources (diesel exhaust, flaming combustion, and smoldering combustion) to illustrate the accuracy with which these ratios can be used to discriminate between particles produced from fires and particles produced from diesel exhausts. These values are shown below in Table 3.

TABLE 3

Sensitivity ratios and angular intensity differences for the three types of aerosols.

| Aerosol Source | ΔCEV/ΔI(15) | ΔCEV/ΔI(30) | ΔCEV/(ΔI(15)−ΔI(30)) | ΔI(15)/M−ΔI(30)/M |
|---|---|---|---|---|
| Diesel Exhaust | 17.1 | 29.8 | 42.5 | 0.0052 |
| Flaming Combustion | 1.05 | 2.37 | 1.94 | 0.0442 |
| Smolder Combustion | 0.147 | 0.315 | 0.279 | 0.0955 |

The values shown in Table 3 indicate that the ratio of ionization chamber sensitivity to angular intensity difference, ΔCEV/(ΔI(15)−ΔI(30)), provides for the greatest discrimination between fire combustion aerosols and DPM, although the ratio, ΔCEV/ΔI(15), is comparable. For these two ratios more than two orders of magnitude separate DPM and aerosols from smoldering fires. More than an order of magnitude separates DPM from aerosols from flaming fires, and even for fire-generated aerosols the ratios for smoldering combustion aerosols are a factor of 7 lower than the ratios for flaming combustion aerosols. This demonstrates that DPM can be discriminated from fire-produced aerosols, and that smoldering combustion aerosols can be discriminated from flaming combustion aerosols. If smoldering combustion aerosols can be discriminated from flaming combustion aerosols, then the stage of combustion can be determined.

From a practical viewpoint, the simple ratios, $\Delta CEV/\Delta I$ (15) or $\Delta CEV/\Delta I(30)$, are simpler to implement in a detection process and may be more reliable than the ratio, $\Delta CEV/(\Delta I(15)-\Delta I(30))$. This is because the latter ratio requires 3 measurements rather than 2 measurements, and additional electronics are needed to subtract the intensities before determining the ratio. The ratios $\Delta CEV/\Delta I(15)$ or $\Delta CEV/\Delta I(30)$ can be used in a detection process of a detector having an ionization chamber and a light-scattering module.

Although less desirable, the intensity difference $\Delta I(15)$ $-\Delta I(30)$ also can be used to discriminate between DPM and combustion aerosols. In this case, there would also be no need for the ionization chamber, thereby resulting in a simpler device.

EXAMPLE #5

Detection Process for Underground Mines

Federal regulations require that when smoke detectors are used for early-warning fire detection in underground coal mines, they shall provide alarm at optical densities less than $0.022$ m$^{-1}$. The optical density D expressed in inverse meters (m$^{-1}$) measured at an average wavelength of 546 nm is calculated from the transmission T of light through the system of aerosol particles via the expression $$D = (1/L)\log(1/T), \quad (10)$$

where the path length L is constant at 1.483 m. The optical density per unit mass concentration is related to the specific extinction $Q_{EXT}$ in units of m$^2$/g by the simple expression $$Q_{EXT} = 2303 \cdot D/M \quad (11)$$

with the mass concentration M in mg/m$^3$.

In addition, for a detector to function reliably the signals from both the ionization sensor and the light-scattering sensor should be greater than their respective noise levels. In previous examples, the noise level of the ionization chamber 12 (expressed as the standard deviation in the steady-state signal) was determined to be +/−0.0157 volts. The noise levels for the light-scattering module 80 at 15° and 30° were similarly determined and found to have values of +/−0.0115 volts and +/−0.005 volts, respectively.

To increase the reliability of a detection process, the voltage signals from the ionization chamber and the light-scattering module are allowed to increase by a voltage equal to 10 times their respective standard deviations as an initial requirement before an alarm condition is reached. For the CEV, I(15), and I(30) voltages, the increases are 0.157, 0.115, and 0.050 volts, respectively.

Measurements of optical density per unit mass concentration for DPM and different combustion aerosols are shown in column 2 of Table 4. Column 3 of Table 4 is the mass concentration at which D=0.022 m$^{-1}$; column 4 of Table 4 is the mass concentration at which the CEV voltage increase equals 10 standard deviations (calculated using the data of column 2 of Table 2); and column 5 of Table 4 is the mass concentration at which the I(15) voltage increase equals 10 standard deviations (calculated using the data of column 3 of Table 2).

TABLE 4

Measurements of optical density per unit mass concentration for diesel exhaust particles and combustion aerosols, along with the expected mass concentration at D = 0.022 m$^{-1}$, the mass concentrations at an increase of 10 standard deviations of the ion chamber CEV, and the mass concentrations at an increase of 10 standard deviations of the 15° intensity.

| Aerosol Source | D/M | M @ D = 0.022 m$^{-1}$ | M @ 10 CEV S.D. = s | M @ 10 I(15) S.D. = s |
|---|---|---|---|---|
| Diesel Exhaust Flaming | 0.00147 | 15.0 | 0.755 | 9.43 |
| No. 2 Diesel Fuel | 0.00417 | 5.3 | 2.97 | 1.30 |
| Pgh Seam Coal | 0.00347 | 6.3 | 3.44 | 1.57 |
| SBR | 0.00395 | 5.6 | 2.30 | 1.18 |
| Douglas Fir | 0.00327 | 6.7 | 1.45 | 1.52 |
| Bond Paper | 0.00195 | 11.3 | 1.25 | 1.75 |
| Smoldering | | | | |
| Pgh Seam Coal | 0.00315 | 7.0 | 5.61 | 0.79 |
| SBR | 0.00253 | 8.7 | 6.24 | 0.54 |
| Douglas Fir | 0.00205 | 10.7 | 7.42 | 0.70 |

If it is assumed that both signals must satisfy the condition of increases equal to 10 standard deviations, then from Table 4, two points are worth noting. First, the mass concentrations in columns 4 and 5 are always less than the values in column 3, meaning that reliable signals occur before a specified alarm value of optical density is reached. Second, for combustion aerosols, with the exception of flaming Douglas fir and flaming bond paper, the mass concentrations at 10 standard deviation increases are greater for the ion chamber than for the light scattering module, and even for these two exceptions, the difference between the two is small.

Finally, if these voltage increases are satisfied as the initial step of the detection process, a second step leading to alarm is, for example, to form the ratio $\Delta CEV/\Delta I(15)$. If this ratio is less than some pre-set value, then the detector will issue an alarm. From column 2 of Table 4, the average ratio is in the range of 1.05 for flaming combustion aerosols, although for flaming bond paper the calculated ratio is 1.904, and for flaming Douglas fir the calculated ratio is 1.433. It follows from these values that a reasonable ratio for discrimination may be in the range of 2.0. This ratio would be approximately 9 times lower than the ratio for DPM, indicating good to excellent discrimination capabilities.

In any event, a detection process that accounts for all of the above requirements includes the following four conditions that must be satisfied before an alarm is activated:

1. The change in CEV from its base value @ zero aerosol concentration must be greater than 10 standard deviations, or 0.157 volts;
2. The change in I(15) from its base value @ zero aerosol concentration must be greater than 10 standard deviations, or 0.115 volts;
3. The ratio, $\Delta CEV/\Delta I(15)$, for these two signals must be <2.0; and
4. The aerosol optical density should be less than 0.022 m$^{-1}$.

Figure 15:
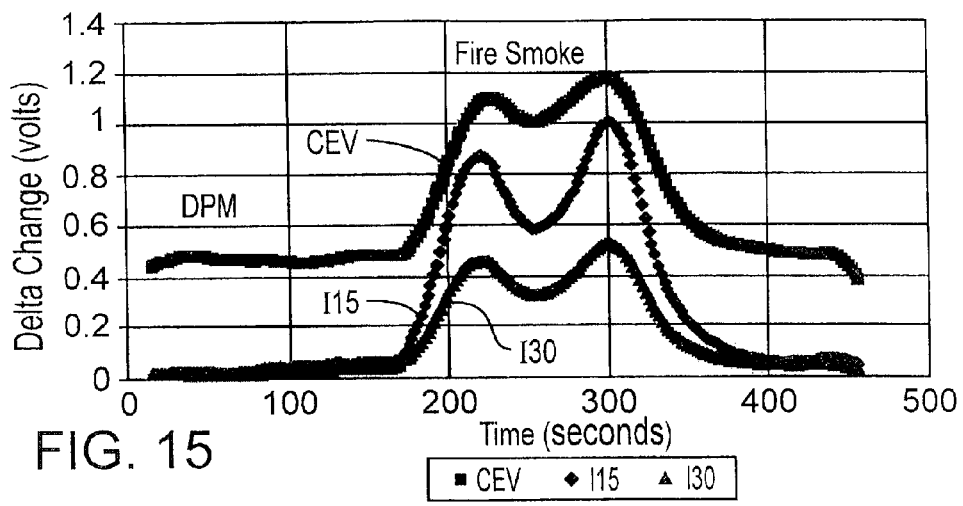
FIG. 15 is a data graph illustrating the responses of the bipolar ionization chamber of FIG. 2 and the light-scattering module of FIG. 6 to flaming combustion aerosols generated in the presence of a pre-existing background of DPM, where the background concentration of DPM is 2.5 mg/m$^3$.
Figure 16:
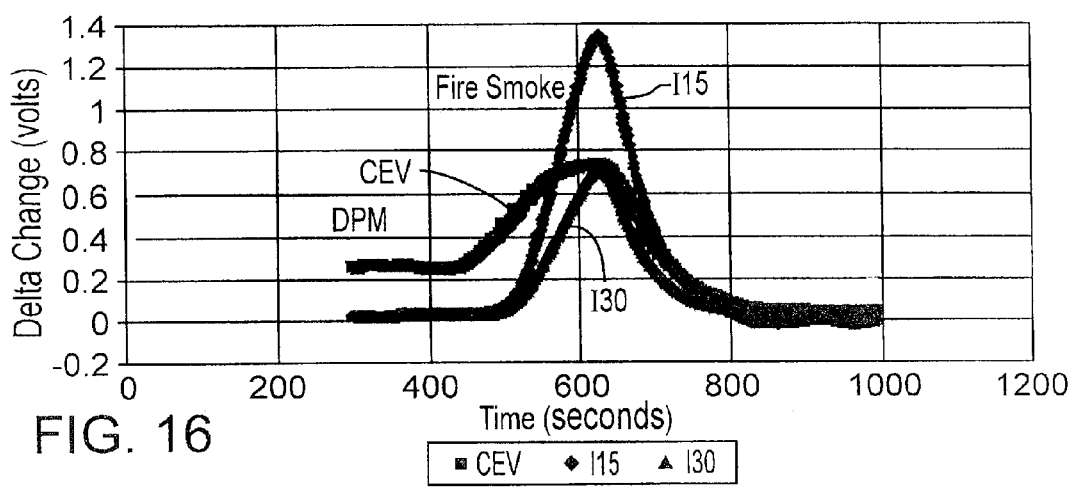
FIG. 16 is a data graph illustrating the responses of the bipolar ionization chamber of FIG. 2 and the light-scattering module of FIG. 6 to smoldering combustion aerosols generated in the presence of a pre-existing background of DPM where the background concentration of DPM is 2.8 mg/m$^3$.
Figure 17:
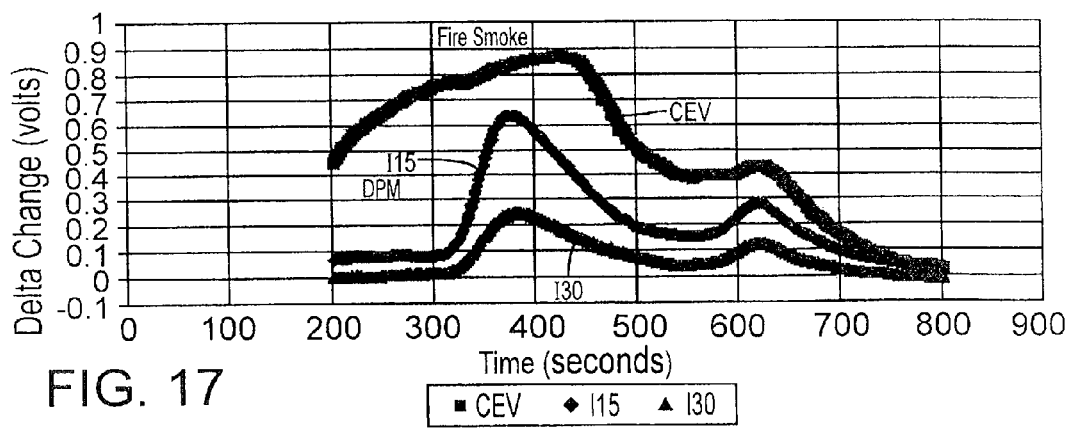
FIG. 17 is a data graph illustrating the responses of the bipolar ionization chamber of FIG. 2 and the light-scattering module of FIG. 6 to smoldering combustion aerosols generated in the presence of a pre-existing background of DPM where the background concentration of DPM is 7.55 mg/m$^3$.

FIGS. 15, 16, and 17 illustrate three examples in which the responses of the bipolar ionization chamber 12 and the light-scattering module 80 were measured to demonstrate this detection process. FIG. 15 illustrates the results of an example for a flaming combustion aerosol where the pre-existing level of DPM was 2.5 mg/m$^3$ with an optical density of 0.0037 m$^{-1}$; FIG. 16 illustrates the results of an example for a smoldering combustion aerosol where the pre-existing level of DPM was 2.8 mg/m$^3$ with an optical density of 0.0041 m$^{-1}$; and FIG. 17 illustrates the results of an example for a smoldering combustion aerosol where the pre-existing level of DPM was 7.55 mg/m$^3$ with an optical density of 0.0094 m$^{-1}$.

In general, all three examples show the same trends. As the combustion aerosol begins to enter the smoke chamber, all three signals begin to increase, with the I(15) and I(30) signals increasing more rapidly than the CEV. In each example, the CEV from DPM is sufficient to satisfy condition 1 above. In the flaming combustion aerosol example (FIG. 15), condition 2 is satisfied 24 seconds after this aerosol begins to enter the smoke chamber; condition 3 is satisfied at 36 seconds where the optical density is 0.020, satisfying condition 4.

In the first smoldering combustion aerosol example (FIG. 16), condition 2 is satisfied 34 seconds after the aerosol initially enters the smoke chamber and condition 3 is satisfied at 56 seconds at an optical density of 0.0135 m$^{-1}$, satisfying condition 4. In the second smoldering combustion aerosol example (FIG. 17), condition 2 is satisfied 32 seconds after the aerosol initially enters the smoke chamber and condition 3 is satisfied at 54 seconds at an optical density of 0.020 m$^{-1}$.

For all three examples, the ratio $\Delta CEV/\Delta I(15)$ in the presence of DPM only was in the range of 15 to 20. In the flaming combustion example, this ratio reached a minimum of 1.17 at a total aerosol concentration of 10.7 mg/m$^3$; in the first smoldering combustion example, the minimum ratio of 0.544 occurred at a total aerosol concentration of 11.3 mg/m$^3$; and in the second smoldering combustion example, the minimum ratio of 1.379 was reached at a total aerosol concentration of 11.2 mg/m$^3$ even though roughly 67% of the total mass was due to DPM.

Figures 18, 19:
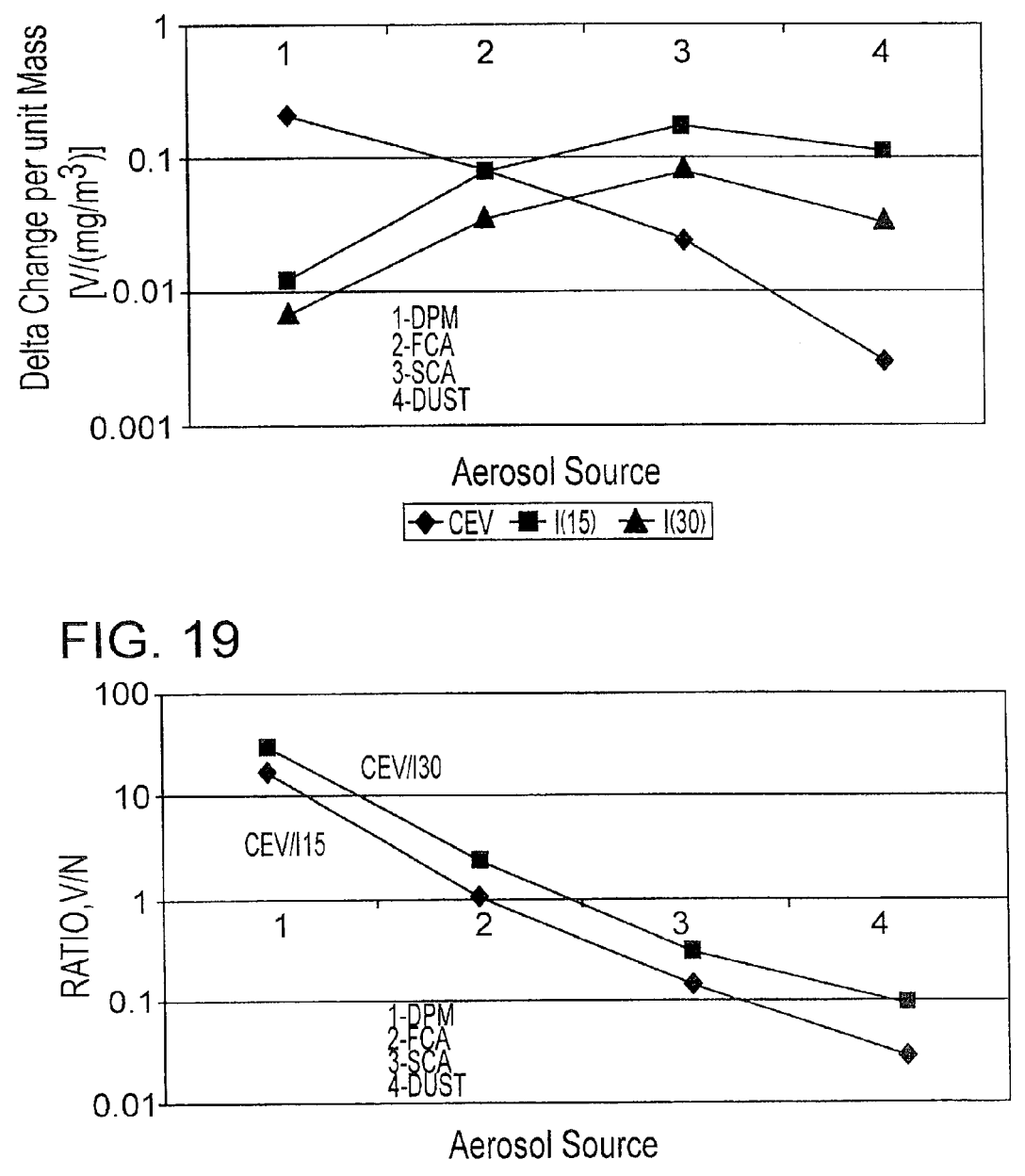

The major results of the foregoing examples are summarized in FIGS. 18 and 19. FIG. 18 illustrates that the sensitivities per unit mass for both the ionization chamber 12 and the light-scattering module 80 plotted as a function of the type of particle. The results are clear and dramatic—the ionization chamber sensitivity decreases with the type of particle while the light-scattering sensitivity increases. These two opposite responses, one decreasing the other two increasing, result in the ratios $\Delta CEV/\Delta I(15)$ and $\Delta CEV/\Delta I(30)$ (shown in FIG. 19) varying by more than 2 orders of magnitude from DPM to smoldering combustion aerosols.

The combination of ionization chamber 12 and light-scattering module 80 was shown to provide excellent discrimination capabilities as a fire sensor for the detection of developing fires in atmospheres contaminated by DPM, both in underground mines or in any other application where similar problems exist. The use of an alarm based upon satisfying three conditions for the sensor signals (the 4$^{th}$ condition is imposed externally) was shown to have merit in situations that are typical of normal usage.

For applications where DPM contamination may not be a problem, the use of either the ionization chamber 12 or the light-scattering module 80 could be used independently, although the light-scattering module 18 offers greater sensitivity to both types of combustion aerosols. Even in applications where DPM contamination is not a problem, the use of a combined sensor (e.g., the dual module 100) allows for the determination of the stage of the combustion process, should the need to make this determination exist.

The invention has been described with respect to particular embodiments and modes of action for illustrative purposes only. The present invention may be subject to many modifications and changes without departing from the spirit or essential characteristics thereof. We therefore claim as our invention all such modifications as come within the scope of the following claims.

We claim:

1. A monitor for measuring the mass concentration of particulate matter in the atmosphere, the monitor comprising:
    an ionization sensor comprising a chamber for receiving a flow of particulate matter and an ionization source for generating ions in the chamber, wherein the ionization sensor is operable to provide an output signal corresponding to an electric potential within the chamber; and
    a controller adapted to receive the output signal from the ionization sensor, the controller being operable to translate the output signal into the mass concentration of particulate matter;
    wherein the ionization source comprises a first field electrode in the chamber and wherein the ionization sensor comprises a second field electrode disposed in the chamber and a sensing electrode disposed between the first and second field electrodes, which measures the electro-static potential in the chamber.

2. The monitor of claim 1, wherein the chamber has an inlet opening and an outlet opening, and a pump operable to produce a flow of particulate matter through the chamber from the inlet opening to the outlet opening.

3. The monitor of claim 1, wherein the controller is configured to display a value for the mass concentration of particulate matter.

4. The monitor of claim 1 configured to measure the mass concentration of diesel particulate matter in the atmosphere.

5. The monitor of claim 1, further comprising a light-scattering sensor operable to provide an output signal corresponding to the mass concentration of particulate matter, and wherein the controller is adapted to receive the output signal from the light-scattering sensor, the controller being operable to translate said output signal into the mass concentration of particulate matter.

6. The monitor of claim 5, wherein:
    the ionization sensor is operable to provide an output signal corresponding to a mass concentration of sub-micrometer particles in the atmosphere;
    the light-scattering sensor is operable to provide an output signal corresponding to the total mass concentration of sub-micrometer particles and respirable dust in the atmosphere; and
    the controller is operable to determine the mass concentration of sub-micrometer particles from the output signal of the ionization sensor, the total mass concentration of sub-micrometer particles and respirable dust from the output signal of the light-scattering sensor, and the mass concentration of respirable dust by subtracting the mass concentration of sub-micrometer particles from total mass concentration of sub-micrometer particles and respirable dust.

7. The chamber of claim 1, wherein the second field electrode comprises an end wall of the chamber.

8. The chamber of claim 1, wherein the chamber has an end wall with an inner surface and wherein the ionization source is positioned on the inner surface of the end wall.

9. A monitor for measuring the mass concentration of diesel particulate matter in the atmosphere, the monitor comprising:
an ionization sensor comprising a chamber for receiving a flow of particulate matter and an ionization source for generating ions in the chamber, wherein the ionization sensor is operable to provide an output signal corresponding to an electric potential within the chamber; and
a controller adapted to receive the output signal from the ionization sensor, the controller being operable to translate the output signal into the mass concentration of particulate matter;
wherein the output signal is a voltage signal and the controller translates the voltage signal into the mass concentration of diesel particulate matter in the ionization module with the expression $m=(\Delta CEV/0.51)^{4.1322}$, where $\Delta CEV$ is a change in voltage detected in the chamber.

10. The monitor of claim 9, wherein the controller further translates the voltage signal into the mass concentration of diesel particulate matter in the ionization module with signal averaging.

11. A monitor for measuring the mass concentration of particulate matter in an atmosphere that comprises respirable dust and sub-micrometer particles, the monitor comprising:
an ionization sensor operable to provide an output signal corresponding to the mass concentration of particulate matter in the atmosphere;
a controller adapted to receive the output signal from the ionization sensor, the controller being operable to translate the output signal into the mass concentration of particulate matter;
a light-scattering sensor operable to provide an output signal corresponding to the mass concentration of particulate matter, and wherein the controller is adapted to receive the output signal from the light-scattering sensor, the controller being operable to translate said output signal into the mass concentration of particulate matter;
wherein the ionization sensor is operable to provide an output signal corresponding to the mass concentration of sub-micrometer particles;
the light-scattering sensor is operable to provide an output signal corresponding to the total mass concentration of sub-micrometer particles and respirable dust; and
the controller is operable to determine the mass concentration of sub-micrometer particles from the output signal of the ionization sensor, the total mass concentration of sub-micrometer particles and respirable dust from the output signal of the light-scattering sensor, and the mass concentration of respirable dust by subtracting the mass concentration of sub-micrometer particles from total mass concentration of sub-micrometer particles and respirable dust.

12. A monitor for measuring the mass concentration of particulate matter in the atmosphere, the monitor comprising:
an ionization sensor comprising a chamber for receiving a flow of particulate matter and an ionization source for generating ions in the chamber, wherein the ionization sensor is operable to provide an output signal corresponding to an electric potential within the chamber,
a controller adapted to receive the output signal from the ionization sensor, the controller being operable to translate the output signal into the mass concentration of particulate matter; and
a light-scattering sensor operable to provide an output signal corresponding to the mass concentration of particulate matter, and wherein the controller is adapted to receive the output signal from the light-scattering sensor, the controller being operable to translate said output signal into the mass concentration of particulate matter;
wherein the light-scattering sensor comprises a light source and at least one light-detecting sensor positioned to detect scattered light at an angle such that the intensity of scattered light varies substantially linearly with the mass concentration of particulate matter minimizing the effects of particle size and particle volatility.

13. The monitor of claim 12, wherein the at least one light-detecting sensor is positioned to detect scattered light at an angle in the range of about 15 to 30 degrees in the forward direction.

14. A monitor for measuring the mass concentration of particulate matter in the atmosphere, the monitor comprising:
an ionization sensor comprising a chamber for receiving a flow of particulate matter and an ionization source for generating ions in the chamber, wherein the ionization sensor is operable to provide an output signal corresponding to an electric potential within the chamber:
a controller adapted to receive the output signal from the ionization sensor, the controller being operable to translate the output signal into the mass concentration of particulate matter; and
an electric insulator in the chamber that separates the interior of the chamber into a first region comprising the ionization source and a second region for receiving the flow of particulate matter.

15. The chamber of claim 14, further comprising a sensing electrode disposed on a top surface of the electric insulator for measuring the electro-static potential in the chamber.

16. The chamber of claim 15, wherein the sensing electrode is positioned in a plane corresponding to a plane of maximum distortion of electrico-static potential in the chamber.

17. A monitor for measuring the mass concentration of particulate matter in the atmosphere, the monitor comprising:
an ionization sensor comprising a chamber and operable to detect a change in the electric potential in the chamber corresponding to the mass concentration of particulate matter in the chamber;
a controller configured to determine the mass concentration of particulate matter based on the change in the electric potential in the chamber; and
a light-scattering sensor operable to detect scattered light in the chamber at an angle such that the intensity of scattered light varies substantially linearly with the total mass concentration of submicrometer particles and respirable dust in the chamber and wherein the controller is configured to determine the total total mass concentration of submicrometer particles and respirable dust based on the intensity of scattered light in the chamber.

18. The monitor of claim 17, wherein:
the controller is configured to determine the mass concentration of respirable dust by subtracting the mass concentration of sub-micrometer particles from the total mass concentration of sub-micrometer particle and respirable dust.

* * * * *